(12) United States Patent
Cho et al.

(10) Patent No.: US 8,748,154 B2
(45) Date of Patent: Jun. 10, 2014

(54) SPHINGOMONAS SP. MICROORGANISM AND METHOD FOR DECOMPOSING METHANE OR ODOR-PRODUCING COMPOUNDS USING THE SAME

(75) Inventors: Kyung Suk Cho, Seoul (KR); Jung Hee Lee, Seoul (KR); Kyung Eun Moon, Incheon (KR); Tae Gwan Kim, Seoul (KR); Sang Hyon Lee, Guri-si (KR)

(73) Assignee: EWHA University-Industry Collaboration Foundation, Seoul (KR)

( * ) Notice: Subject to any disclaimer, the term of this patent is extended or adjusted under 35 U.S.C. 154(b) by 0 days.

(21) Appl. No.: 13/702,745

(22) PCT Filed: Mar. 25, 2011

(86) PCT No.: PCT/KR2011/002071
§ 371 (c)(1),
(2), (4) Date: Jan. 4, 2013

(87) PCT Pub. No.: WO2012/111875
PCT Pub. Date: Aug. 23, 2012

(65) Prior Publication Data
US 2013/0316436 A1 Nov. 28, 2013

(30) Foreign Application Priority Data
Feb. 15, 2011 (KR) .................. 10-2011-0013335

(51) Int. Cl.
C12N 1/12 (2006.01)
C12N 1/20 (2006.01)
A62D 3/00 (2006.01)
C12M 1/00 (2006.01)

(52) U.S. Cl.
USPC .............. 435/252.1; 435/252.4; 435/262.5; 435/283.1

(58) Field of Classification Search
None
See application file for complete search history.

(56) References Cited

FOREIGN PATENT DOCUMENTS

| JP | 2000-246710 A | 2/2002 |
| JP | 2004-367526 A | 6/2006 |
| KR | 1020000047959 B1 | 1/2001 |
| KR | 100963053 B1 | 6/2010 |
| WO | 2009/125462 A1 | 10/2009 |

OTHER PUBLICATIONS

Journal of Life Science, vol. 19, No. 5, pp. 659-663, 2009.
Hyunjung Park, Ewha Womans University, Masters Degree thesis project, Jul. 2010.

*Primary Examiner* — Jennifer McDonald
*Assistant Examiner* — Qing Xu
(74) *Attorney, Agent, or Firm* — Benjamin Aaron Adler

(57) ABSTRACT

The present invention relates to a *Sphingomonas* sp. MD2 strain (KCTC 11845BP), a composition including the strain for decomposing methane or odor-producing compounds, a biocover or biofilter including the composition, a method for decomposing methane or odor-producing compounds using the composition, a system for decomposing methane or odor-producing compounds using the biocover or biofilter, and the use of the strain for decomposing methane or odor-producing compounds. According to the present invention, methane and odor can be effectively removed concurrently, and thus the cost required for the separate treatment of methane and odor can be reduced, and methane and odor-producing compounds in landfills or the like can be effectively decomposed.

19 Claims, 17 Drawing Sheets

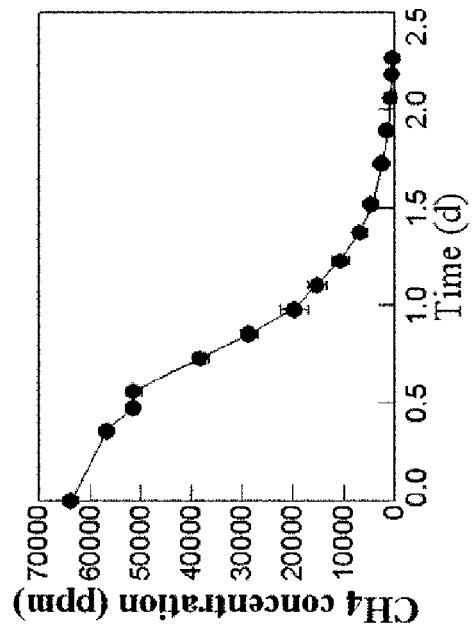
FIG. 3B
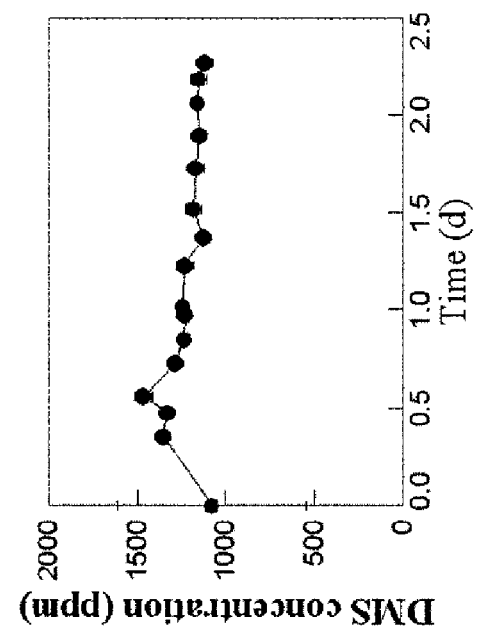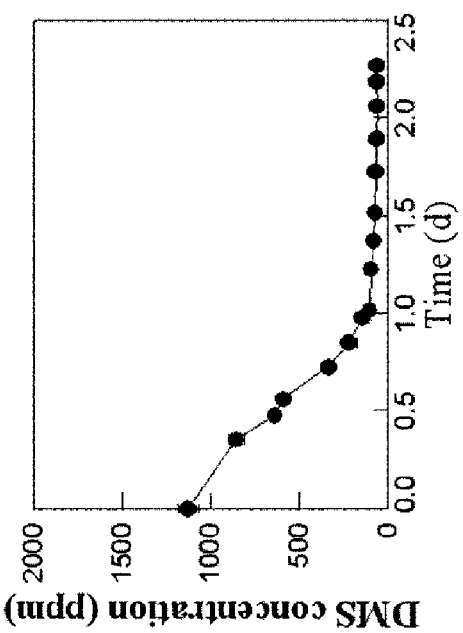
FIG. 3D
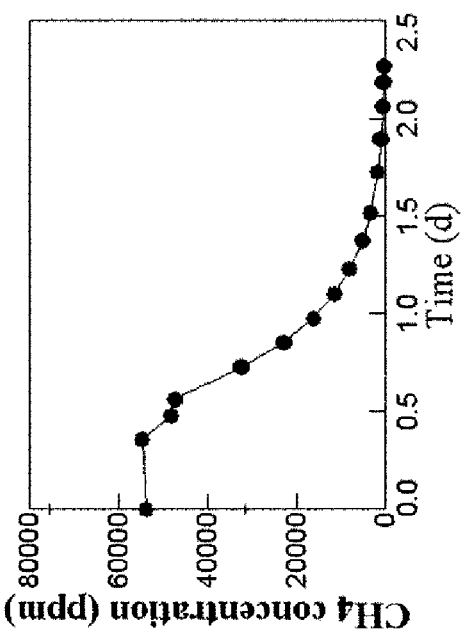
FIG. 3A
FIG. 3C

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: primer 27F for PCR

<400> SEQUENCE: 1
agagtttgat cmtggctcag                                              20

<210> SEQ ID NO 2
<211> LENGTH: 20
<212> TYPE: DNA
<213> ORGANISM: Artificial Sequence
<220> FEATURE:
<223> OTHER INFORMATION: primer 1492R for PCR

<400> SEQUENCE: 2
tacggytacc ttgttacgac                                              20

<210> SEQ ID NO 3
<211> LENGTH: 1382
<212> TYPE: DNA
<213> ORGANISM: Sphingomonas species MD2 strain
<220> FEATURE:
<221> NAME/KEY: rRNA
<223> OTHER INFORMATION: 16S rDNA sequence of Sphingomonas sp. MD2
      strain
<220> FEATURE:
<221> NAME/KEY: rRNA
<222> LOCATION: (35, 41)
<223> OTHER INFORMATION: n is any

<400> SEQUENCE: 3
```

-continued

```
ggcatgccta cacatgcagt cgaacgagat ccttncggat nctagtggcg cacgggtgcg      60
taacgcgtgg gaatcctgcc ctttgggtac ggaataactc agtagaaatt tgtgctaata     120
ccgtataatg tcttcggacc aaagatttat cgcccaagga tgagcccgcg taggattagc     180
tagttggtga ggtaaaagct caccaaggcg acgatcctta gctggtctga gaggatgatc     240
agccacactg ggactgagac acggcccaga ctcctacggg aggcagcagt ggggaatatt     300
ggacaatggg cgaaagcctg atccagcaat gccgcgtgag tgatgaaggc cctagggttg     360
taaagctctt ttacccggga tgataatgac agtaccggga gaataagctc cggctaactt     420
cgtgccagca gccgcggtaa tacgagggga gctagcgttg ttcggaatta ctgggcgtaa     480
agcgcgcgta ggcggttttt taagtcagag gtgaaagccc ggggctcaac cccggaatag     540
cctttgaaac tggaaaacta gaatcttgga gaggtcagtg gaattccgag tgtagaggtg     600
aaattcgtag atattcggaa gaacaccagt ggcgaaggcg actgactgga caagtattga     660
cgctgaggtg cgaaagcgtg gggagcaaac aggattagat accctggtag tccacgccgt     720
aaacgatgat aactagctgt ccgggctcat agagcttggg tggcgcagct aacgcattaa     780
gttatccgcc tggggagtac ggtcgcaaga ttaaaactca aaggaattga cggggccctg     840
cacaagcggt ggagcatgtg ggtttaattc gaagcaacgc gcagaacctt accagcgttt     900
gacatcctga tcgcggttac cagagatggt ttccttcagt tcggctggat cagtgacagg     960
tgctgcatgg ctgtcgtcag ctcgtgtcgt gagatgttgg gttaagtccc gcaacgagcg    1020
caaccctcat ccctagttgc catcattaag ttgggcactc taaggaaact gccggtgata    1080
agccggagga aggtggggat gacgtcaagt cctcatggcc cttacgcgct gggctacaca    1140
cgtgctacaa tggcggtgac agtgggcagc aacctcgcga gaggtagcta atctccaaaa    1200
gccgtctcag ttcggattgt tctctgcaac tcgagagcat gaaggcggaa tcgctagtaa    1260
tcgcggatca gcatgccgcg gtgaatacgt tcccaggcct tgtacacacc gcccgtcaca    1320
ccatgggagt tggtttcacc cgaaggcagt gctctaaccc gcaagggagg aagctgacca    1380
cg                                                                   1382
```

SPHINGOMONAS SP. MICROORGANISM AND METHOD FOR DECOMPOSING METHANE OR ODOR-PRODUCING COMPOUNDS USING THE SAME

BACKGROUND OF THE INVENTION

1. Field of the Invention

The present invention relates to a *Sphingomonas* sp. MD2 strain (KCTC 11845BP), a composition including the strain for decomposing methane or odor-producing compounds, a biocover or biofilter including the composition, a method for decomposing methane or odor-producing compounds using the composition, a system for decomposing methane or odor-producing compounds using the biocover or biofilter, and the use of the strain for decomposing methane or odor-producing compounds.

2. Description of the Related Art

Under anaerobic conditions, organic materials are finally converted into methane and carbon dioxide by microbial decomposition with the release of odor-producing compounds such as hydrogen sulfide, methanethiol (MT), dimethyl sulfide (DMS), ammonia, amine, fatty acids or the like. Therefore, organic waste treatment facilities and processes such as landfills, food waste treatment facilities, anaerobic digestion, and livestock barns are known as the foremost sources for the emission of methane and producing odor concurrently. Of them, landfills are one of the most foremost sources of methane and odor emission, and there were 227 landfills in Korea in 2007 (Ministry of Environment, Resource and Recirculation Bureau, 2007), and the total area of landfills and the volume of landfills were 29,213,000 $m^2$, and 379,416,000 $m^3$, respectively. Evaluated by the gas treatment capacity of these landfills, the landfills equipped with facilities capable of capturing emitted gas for the extraction and subsequent reuse as alternative energy of high concentrations of methane account for only 4% (10 landfills) of the total number of landfills, and most landfills (199 landfills, 89%) emit landfill gas directly into the atmosphere.

Methane is a major greenhouse gas, second only to carbon dioxide, and accounts for 18% of radiative forcing. Since methane concentration in the atmosphere has more than doubled since the industrial era, many studies have focused on the sources and sinks for methanogens or related microorganisms (Bodelier et al., FEMS Microbiol. Ecol. 52, 163-174, 2005). In addition, prior studies have focused on the distribution and diversity of methane-oxidizing microbial communities that play an important role in the global carbon cycle (Bodelier et al., FEMS Microbiol. Ecol. 52, 163-174, 2005).

Landfills are the largest source of methane emissions, and are estimated to account for approximately 35% of anthropogenic methane emissions in US, and 5~10% of global methane in the atmosphere (IPCC, 2001; Stern et al., Waste Manage. 27, 1248-1258, 2007). The representative technologies associated with reduction of methane gas generation during waste treatment are landfill gas capturing and resource recycling technologies, but it is difficult to apply these technologies to inefficient landfills and in cases of emission of low concentrations of methane.

The odor emitted from organic waste treatment facilities such as landfills, food waste treatment facilities, and livestock waste treatment facilities is also a main cause of civil complaints. Reportedly, civil complaints about odor emitted from organic waste treatment facilities account for 60% of the civil complaints about odor in public facilities in 2006 (Ministry of Environment, Air Quality Management Bureau, 2006), and 32% of the civil complaints about the odor emitted from organic waste treatment facilities was related to landfill odors (Ministry of Environment Air Quality Management Bureau, 2006). Landfill odors are produced by a variety of sources. Of them, hydrogen sulfide is the primary cause of odor, and its concentration and emission rate are known to be 0.7~1463.5 mg/$m^3$, and 0.3~633.5 mg·$m^{-2}$·$h^{-1}$, respectively. According to a recent survey of landfill odors in Korea, terrible odor is caused by the emission of landfill gas through cracks or holes in landfill layers and cover layers, and the odor concentration in the landfill gas that was emitted through the cracks at the surface of landfill cover was approximately 17,000 as a dilution ratio, and the concentration of hydrogen sulfide was 400,000 ppb or higher. When waste is compressed by a compressor, landfill gas moves to the outer slope of the landfill. Thus, odor management for the outer slopes of landfills is also needed.

Odor management in organic waste treatment facilities or processes, such as landfills, is mainly conducted by odor measurement and monitoring, with passive management such as the use of deodorizers only being conducted for odor suppression. Given the future compulsory regulatory disclosure of odor management capability and equipment by public works facilities such as landfills, manure treatment facilities, and other organic waste treatment facilities, there is an existing need for novel technologies addressing the root sources of odor.

Recently, various odor reduction techniques such as the use of landfill covers having odor reduction effects, placement of on-site biofilters on cracks, and placement of portable biofilters in landfill gas wells have been proposed. However, the techniques are not actively utilized for odor reduction, because of their high cost and low efficiency. In particular, odor management techniques have been very actively developed as compared with methane reduction techniques, and a variety of odor management and control techniques such physical, chemical, biological, and hybrid techniques have been developed and commercialized. However, with respect to economic aspects such as installation cost and running expense, the conventional odor reduction techniques are not suitable in application to large areas including landfills. Therefore, the issues resulting from odor in these sources have not been solved yet.

Accordingly, reduction of both odor and methane emissions will create a new economic effect of earning carbon emission credits corresponding to the methane reduction, which offsets the costs required for applying only the odor reduction techniques. It is also expected that the efficiency of land use can be improved by solving the odor byproduct of waste treatment facilities such as landfills, which can contribute to national industrial competitiveness through the bolstering or creation of related industries.

Given this background, the inventors of the present invention have made many efforts to develop a technique for removing both methane and odor that are generated from landfills or the like, and they found that a novel *Sphingomonas* sp. strain is able to remove methane and odor-producing compounds concurrently, thereby completing the present invention.

SUMMARY OF THE INVENTION

An object of the present invention is to provide a *Sphingomonas* sp. MD2 strain (KCTC 11845BP).

Another object of the present invention is to provide a composition including the *Sphingomonas* sp. MD2 strain (KCTC 11845BP) for decomposing methane or odor-producing compounds.

Still another object of the present invention is to provide a biocover including the composition for decomposing methane or odor-producing compounds.

Still another object of the present invention is to provide a biofilter including the composition for decomposing methane or odor-producing compounds.

Still another object of the present invention is to provide a method using the composition for decomposing methane or odor-producing compounds.

Still another object of the present invention is to provide a system for decomposing methane or odor-producing compounds, in which a bioactive layer including a biocover layer formed by laminating one or more biocovers; and a ventilating layer surrounding the biocover layer or a ventilating layer laminated on the lower surface of the biocover layer is provided at the source of the generation of methane or odor-producing compounds to biologically decompose methane or odor-producing compounds.

Still another object of the present invention is to provide a system for decomposing methane or odor-producing compounds, in which a bioactive layer including a biofilter layer formed by laminating one or more biofilters; and a ventilating layer surrounding the biofilter layer or a ventilating layer laminated on the lower surface of the biofilter layer is provided at the source of the generation of methane or odor-producing compounds to biologically decompose methane or odor-producing compounds.

Still another object of the present invention is to provide a use for the *Sphingomonas* sp. MD2 strain (KCTC 11845BP) in the decomposing of methane or odor-producing compounds.

BRIEF DESCRIPTION OF THE DRAWINGS

FIGS. 3A-3D are graphs showing the methane and DMS decomposition characteristics of the *Sphingomonas* sp. MD2, in which (FIG. 3A) shows the results given the injection of methane only, (FIG. 3B) and (FIG. 3C) show the results given the injection of both methane and DMS, and (FIG. 3D) shows the results given the injection of DMS only;

DETAILED DESCRIPTION OF THE PREFERRED EMBODIMENTS

In one aspect to achieve the above objects, the present invention provides a *Sphingomonas* sp. MD2 strain (KCTC 11845BP).

The *Sphingomonas* sp. MD2 strain (KCTC 11845BP) of the present invention is a microorganism that was newly identified by the present inventors, and is able to decompose methane as well as odor-producing compounds including dimethyl sulfide and hydrogen sulfide.

The present inventors sealed culture bottles containing enrichment medium and soil samples from landfills and swamps, and injected methane and DMS as a carbon source, and continuously supplied nitrogen and phosphorus during cultivation. Then, they used the enrichment medium as an inoculation medium, and isolated a novel methane-oxidizing bacterium having excellent ability to decompose methane and odor-producing compounds, and extracted DNA from the strain thereof. The result of 16S rDNA gene fragment analysis showed that the strain belongs to the genus *Sphingomonas*. This microorganism capable of decomposing methane and odor-producing compounds concurrently was designated as MD2 strain (Table 1 and FIG. 1). The *Sphingomonas* sp. MD2 strain was deposited at the Biological Resource Center, Korea Research Institute of Bioscience and Biotechnology on Jan. 6, 2011 under the accession number KCTC 11845BP.

Figure 2:
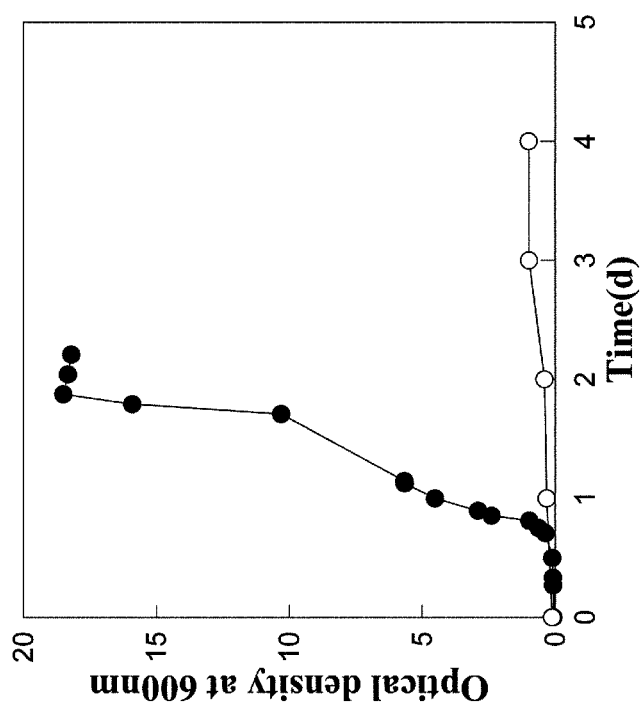
FIG. 2 is a graph showing a comparison of the growth curve between the known methane-oxidizing bacterium M6 and the MD2 strain.

Further, the growth rate of the *Sphingomonas* sp. MD2 strain of the present invention was compared to that of the known methane-oxidizing bacterium, *Methylocystis* sp. M6 (KCTC 11519BP). As a result, when the *Methylocystis* sp. M6 strain was cultured for 4 days, the absorbance at 600 nm was increased to 1. In contrast, the *Sphingomonas* sp. MD2 strain is a heterotrophic bacterium utilizing complex substrates as a carbon source, and within 2 days after cultivation, its absorbance at 600 nm measured after dilution was increased to approximately 18 (FIG. 2). These results showed that the *Sphingomonas* sp. MD2 strain of the present invention can be easily mass-cultured by using inexpensive substrates such as organic waste in a short period of time, and thus applied to various industries, whereas the conventional methane-oxidizing bacterium has very low growth rate and the risk of combustion consequently becomes a factor, and additionally its viability for mass-production in industrial application is also limited because of the utilization of expensive methane gas as a substrate.

In another aspect, the present invention provides a composition for decomposing methane or odor-producing compounds, including the *Sphingomonas* sp. MD2 strain (KCTC 11845BP).

The composition of the present invention includes the *Sphingomonas* sp. MD2 strain (KCTC 11845BP) capable of decomposing methane and odor-producing compounds at the same time, thereby being effectively used for decomposing methane or odor-producing compounds.

As used herein, the odor-producing compounds are materials that cause unpleasant feelings resulting from stimulation of the sense of smell of animals including human, and odor is additionally known to cause loss of appetite, dyspnoea, motion sickness and vomiting, leading to mental confusion.

The odor-producing compounds may be, but are not limited to, one or more compounds selected from the group consisting of ammonia, methyl mercaptan, hydrogen sulfide, dimethyl sulfide, dimethyl disulfide, trimethyl amine, acetaldehyde, styrene. propionaldehyde, butyraldehyde, n-valeraldehyde, i-valeraldehyde, toluene, benzene, xylene, methyl ethyl ketone, methyl isobutyl ketone and butyl acetate, and preferably one or more compounds selected from the group consisting of hydrogen sulfide, methyl mercaptan, dimethyl sulfide, benzene and toluene.

The composition for decomposing methane or odor-producing compounds of the present invention may include a typical medium for culturing the *Sphingomonas* sp. MD2 strain of the present invention. The composition of the present invention may also include one or more fillers selected from the group consisting of soil, activated carbon, decomposed granite soil, and earthworm casting, in order to create the culture environment for bacterial growth.

The soil may be, but is not limited to, paddy/field soil, forest soil, or wetland soil, and the soil can be sampled at a depth of 10 to 200 cm from the surface, with the large particles filtered through a sieve having perforations of 2 mm or smaller.

The earthworm casting is a mixture of various enzymes secreted by earthworms, minerals, undigested worm foods, and ammonia excreted by the earthworm's intestine. For production of earthworm casting, sewage sludge produced during sewage treatment is fed to earthworms, and the earthworm castings produced are subjected to a natural fermentation/drying process for 6 months or longer. After removing impurities, the earthworm casting having a particle size of 0.2 to 2 mm can be used.

It is apparent that the proper type and quantify of the filler included in the composition for decomposing methane or odor-producing compounds of the present invention are selected by those skilled in the art according to all circumstances such as the environment where methane or odor-generating sources are found, the type and amount of odor-producing compounds, and the circumstances of the environment and conditions.

The composition for decomposing methane or odor-producing compounds of the present invention may further include typical methane-oxidizing bacteria in order to increase the decomposition efficiency of methane. The methane-oxidizing bacteria may include one, or two or more of *Methylomonas, Methylomicrobium, Methylobacter, Methylocaldum, Methylophaga, Methylosarcina, Methylothermus, Methylohalobius, Methylosphaera, Methylocystis, Methylocella, Methylocapsa, Methylosinus*, and *Methylococcus*.

In still another aspect, the present invention provides a biocover for decomposing methane or odor-producing compounds, including the composition including the *Sphingomonas* sp. MD2 strain (KCTC 11845BP) for decomposing methane or odor-producing compounds.

The composition for decomposing methane or odor-producing compounds of the present invention is put in the biocover for decomposing methane or odor-producing compounds, and the biocover is installed at the source of generation of methane or odor-producing compounds to have contact with methane or odor-producing compounds, thereby effectively decomposing the methane or odor-producing compounds.

The biocover of the present invention may include a biomedia layer that includes the composition for decomposing methane or odor-producing compounds of the present invention, and the biomedia layer includes the *Sphingomonas* sp. MD2 strain (KCTC 11845BP) capable of biologically decomposing methane and odor-producing compounds concurrently.

The biomedia layer may further include the conventional methane-oxidizing bacteria in order to increase the decomposition efficiency of methane, and the type of the methane-oxidizing bacteria is the same as described above.

Further, the biomedia layer may include one or more fillers selected from the group consisting of soil, activated carbon, decomposed granite soil, and earthworm casting, in order to create the culture environment for bacterial growth.

The biomedia layer may further include an oxygen releasing compound to reduce the thickness of the biocover by supplying oxygen required by microorganisms such as *Sphingomonas* sp. MD2 strain (KCTC 11845BP). Examples thereof may include, but are not limited to, one or more of the oxygen releasing compounds selected from the group consisting of magnesium peroxide, calcium peroxide and sodium percarbonate.

In still another aspect, the present invention provides a biofilter for decomposing methane or odor-producing compounds, including the composition for decomposing methane or odor-producing compounds including the *Sphingomonas* sp. MD2 strain (KCTC 11845BP).

The composition for decomposing methane or odor-producing compounds of the present invention is put in a support within the biofilter, and the biofilter is installed at the source of the generation of methane or odor-producing compounds to filter the methane or odor-producing compounds, thereby effectively decomposing the methane or odor-producing compounds.

The biofilter of the present invention may include a support that includes the composition for decomposing methane or odor-producing compounds of the present invention, and the support is used for adhesion and growth of the *Sphingomonas* sp. MD2 strain decomposing methane and odor-producing compounds of the present invention, and examples thereof may be, but are not limited to, soil, earthworm casting, peat moss, activated carbon fiber, polyurethane, diatomite earth, basalt, fibrous support, polymer foam or porous ceramic, orchid stone and activated carbon. They may be used alone or in combination. Preferably, orchid stone and activated carbon may be used in combination. More preferably, orchid stone with a diameter of 5 to 10 mm and activated carbon with a diameter of 4 to 8 mm may be used in combination.

The biofilter may further include an oxygen releasing compound to reduce the thickness of the biofilter by supplying oxygen required by microorganisms such as *Sphingomonas* sp. MD2 strain (KCTC 11845BP). Examples thereof may include, but are not limited to, one or more of the oxygen releasing compounds selected from the group consisting of magnesium peroxide, calcium peroxide and sodium percarbonate.

In still another aspect, the present invention provides a method for decomposing methane or odor-producing compounds using the composition of the present invention. Specifically, the decomposition method may include the steps of treating the source of the generation of methane or odor-producing compounds with the composition of the present invention; and decomposing the methane or odor-producing compounds by way of the composition.

The sources of generating methane or odor-producing compounds may be, but are not limited to, scrap landfills, waste landfills, wastewater treatment facilities, manure treatment facilities, livestock wastewater treatment facilities, food waste treatment facilities, petrochemical product manufacturing factories, sewage treatment facilities, industrial wastewater treatment facilities, livestock farms, food processing plants, paint manufacturing plants, casting manufacturing plants, petroleum refining facilities, slaughterhouses, fertilizer producing factories, combustion facilities for plastic product manufacture, coating facilities or plating factories.

In still another aspect, the present invention provides a system for decomposing methane or odor-producing compounds, in which the bioactive layer including the biocover layer formed by laminating one or more biocovers; and a ventilating layer surrounding the biocover layer or a ventilating layer laminated on the lower surface of the biocover layer is provided at the source of the generation of methane or odor-producing compounds to biologically decompose methane or odor-producing compounds.

In still another aspect, the present invention provides a system for decomposing methane or odor-producing compounds, in which the bioactive layer including the biofilter layer formed by laminating one or more biofilters; and a ventilating layer surrounding the biofilter layer or a ventilating layer laminated on the lower surface of the biofilter layer is provided at the source of the generation of methane or odor-producing compounds to biologically decompose methane or odor-producing compounds.

The source of the generated methane or odor-producing compounds may be, as described above, scrap landfills, waste landfills, wastewater treatment facilities, manure treatment facilities, livestock wastewater treatment facilities, food waste treatment facilities, petrochemical product manufacturing factories, sewage treatment facilities, industrial wastewater treatment facilities, livestock farms, food processing plants, paint manufacturing plants, casting manufacturing plants, petroleum refining facilities, slaughterhouses, fertilizer producing factories, combustion facilities for plastic product manufacture, coating facilities or plating factories.

The biocover layer and the biofilter layer include the Sphingomonas sp. MD2 strain of the present invention, thereby biologically decomposing methane or odor-producing compounds.

The biocover layer and the biofilter layer may further include the typical methane-oxidizing bacteria as described above.

The biocover layer may include one or more selected from the group consisting of soil, activated carbon, decomposed granite soil, and earthworm casting as a filler, in order to increase the oxidation efficiency of the methane and odor-producing compounds. Preferably, the biocover layer may include soil, activated carbon, earthworm casting and decomposed granite soil, and more preferably, soil, activated carbon, earthworm casting and decomposed granite soil at a weight ratio of 4:2:1:1.

The biofilter layer may include a support including the composition for decomposing methane or odor-producing compounds of the present invention, and the support may be, but is not limited to, soil, earthworm casting, peat moss, activated carbon fiber, polyurethane, diatomite earth, basalt, fibrous support, polymer foam or porous ceramic, orchid stone and activated carbon. They may be used alone or in combination. Preferably, orchid stone and activated carbon may be used in combination. More preferably, orchid stone with a diameter of 5 to 10 mm and activated carbon with a diameter of 4 to 8 mm may be used in combination.

The thickness of the biocover layer is preferably 20 to 100 cm. If the thickness is less than 20 cm, the time of contact of the methane-oxidizing bacteria with the methane gas is short. Thus, sufficient oxidation does not occur, and methane gas is not converted into carbon dioxide. If the thickness is more than 100 cm, oxygen in the atmosphere does not reach the lower surface of the biocover layer, and thus aerobic conditions cannot take place.

The biocover layer and the biofilter layer are surrounded by the ventilating layer for supplying oxygen, and the constituent of the ventilating layer is not particularly limited, as long as it has a particle size capable of supplying oxygen. For example, the ventilating layer may be composed of sands or pebbles. One or more ventilation ducts for supplying air may be installed in the ventilating layer, and air can be injected through the ventilation duct using a ventilator.

In still another aspect, the present invention provides use of the Sphingomonas sp. MD2 strain (KCTC 11845BP) for decomposing methane or odor-producing compounds.

The Sphingomonas sp. MD2 strain of the present invention is able to effectively remove methane as well as odor at the same time, and thus can be used in landfills to reduce the costs required for the separate treatment of methane and odor and to effectively decompose methane and odor-producing compounds at the same time.

Hereinafter, the present invention will be described in more detail with reference to Examples and Comparative Examples. However, these Examples are for illustrative purposes only, and the invention is not intended to be limited by these Examples,

EXAMPLE 1

Acquisition of Microbial Consortia for Decomposing Methane and Odor-Producing Compounds at the Same Time In order to obtain enriched culture broth for decomposing methane and odor-producing compounds (hereinafter, used interchangeably with "odor") concurrently, soil was sampled at landfills and swamps. The soil was sampled at a depth of approximately 10 cm below the surface of the landfill cover at Gongju-si and Gapyeong-gun. In addition, the soil was also sampled at a depth of approximately 10 cm below the surface of the Geum river wetland at Gongju-si. The soil sampled was sieved through a 2 mm-sieve, and small particles were selected and then stored at 4° C. before use.

To obtain microbial consortia capable of decomposing methane and odor concurrently, enrichment culture was performed as follows. The soils sampled at the landfills of Gongju-si and Gapyeong-gun and at the wetland were mixed at an equal weight ratio, and the mixed soil was then inoculated, 20 ml of nitrate mineral salt medium (NMS medium; $MgSO_4 7H_2O$ 1 g/L; $CaCl_2 2H_2O$ 0.295 g/L; $KNO_3$ 1 g/L; $KH_2PO_4$ 0.26 g/L; $Na_2HPP_4 12H_2O$ 0.41 g/L) and 8 g (wet weight) of the mixed soil was added to a 600 ml-serum bottle.

The bottle was sealed with a butyl rubber septum. Methane gas was injected into the sealed serum bottle to a final concentration of 5% (v/v) from a methane gas cylinder (99% v/v, Dong-A gases, Korea) using a gaslight syringe. 2 µl of a DMS solution (99%, Acros Organics, USA) was also injected using a micro syringe. After injection of methane and DMS, the serum bottles were incubated at 30° C. with shaking at 200 rpm, and 0.3 ml of the gases in the headspace of each serum bottle was sampled every other day using a gas-tight syringe and analyzed via gas chromatography (Agilent 6890 plus, USA) equipped with a flame ionization detector (FID) to measure the methane and DMS residual concentrations. When the methane and DMS concentrations in the serum bottle dropped below a detection limit (methane 20 ppm, DMS 5 ppm), each serum bottle was opened for supplying oxygen, and left to allow the gases inside the bottle to be replaced with air. Each bottle was then re-sealed. After methane gas and DMS had been re-injected at the same concentration as described above, the bottle was re-incubated under the same conditions as described above. The injections were repeated in this way a further 5 times. To prevent exhaustion of nitrogen and phosphorous sources during the incubation, each 1 ml of concentrated nitrogen solution ($KNO_3$ 20 g/L, $KH_2PO_4$ 5.2 g/L) and concentrated phosphorous solution ($Na_2HPO_4 12H_2O$ 18.5 g/L) was separately added to the serum bottles every second injection.

EXAMPLE 2

Isolation and Identification of Bacteria having an Ability to Decompose Methane and Odor-Producing Compounds In order to isolate a strain capable of decomposing methane and odor at the same time, the enriched culture medium was inoculated to isolate the pure strain. 1 ml of the enriched culture medium was diluted in 9 ml of 0.9% NaCl solution, and then the diluted solution was serially diluted 1/10-fold in the 0.9% NaCl solution. Each of the diluted solutions was plated on an NMS-agar plate (prepared by adding 15 g/L of agar to NMS medium). A 5 L-desiccator was sterilized using 70% ethanol, and then the plated NMS-agar plates were placed in the desiccator. After injection of 250 ml of methane gas (99%) and 16.7 µl of DMS (99%) through the cover of the desiccator, the plates were cultured in the stationary phase at 30° C. to observe the growth of the strain. Seven types of colonies were selected according to the shape and color of the colonies. Each colony was streaked on a Difco™ R2A agar plate (Becton, Dickinson and Company, USA, Yeast extract 0.5 g/L; Proteose Peptone No. 3 0.5 g/L; Casamino Acids 0.5 g/L; Dextrose 0.5 g/L; Soluble Starch 0.5 g/L; Sodium Pyruvate 0.3 g/L; Dipotassium Phosphate 0.3 g/L; Magnesium sulfate 0.05 g/L; Agar 15.0 g/L), and then cultured in the stationary phase at 30° C. to observe the growth of one type of colony on each plate.

it was confirmed that seven types of colonies were pure strains. Then, each colony was mass-cultured in an R2A agar medium, and the strains were collected and inoculated in serum bottles containing 4 ml of NMS medium. The bottles were sealed with a butyl rubber septum. Methane was injected to a final concentration of 5% (v/v), and 2 µl of DMS solution was injected. The methane and DMS concentrations in the headspace of each serum bottle were analyzed according to time. Of the 7 types of strains selected, 2 strains showing an ability to oxidizing methane and DMS were selected, and 1 strain showing a higher activity was selected and designated as MD2.

In order to identify MD2 which is a pure strain capable of decomposing methane and odor concurrently, the strain was cultured in the NMS medium injected with methane and DMS as a sole carbon source for 26 days. 1 ml of the culture broth was centrifuged at 14,000×g for 5 minutes, and DNA was extracted from the obtained strain using a BIO101 FastDNA SPIN Kit (MP Biomedicals LLC, Solon, USA) for soil according to the instructions. The extracted DNA was amplified using 27f (SEQ ID NO. 1; 5'-AGA GTT TGA TCM TGG CTC AG-3') and 1492r (SEQ ID NO. 2; 5'-TAC GGY TAC CTT GTT ACG AC-3'). The amplification was performed under the following conditions: initial denaturation at 95° C. for 5 minutes, followed by 30 cycles of denaturation at 96° C. for 1 minute, annealing at 58° C. for 30 seconds and elongation at 72° C. for 1 minute and 45 seconds, with a final elongation step at 72° C. for 10 minutes. After amplification, the product was maintained at 4° C. The amplified DNA was purified using a QIAquick PCR purification kit (QIAGEN GnH, Hilden, Germany), followed by sequencing analysis. The base sequences were compared with GenBank database using a Basic Local Alignment Search Tool (BLAST) algorithm, thereby searching a strain showing the highest similarity.

Figure 1:
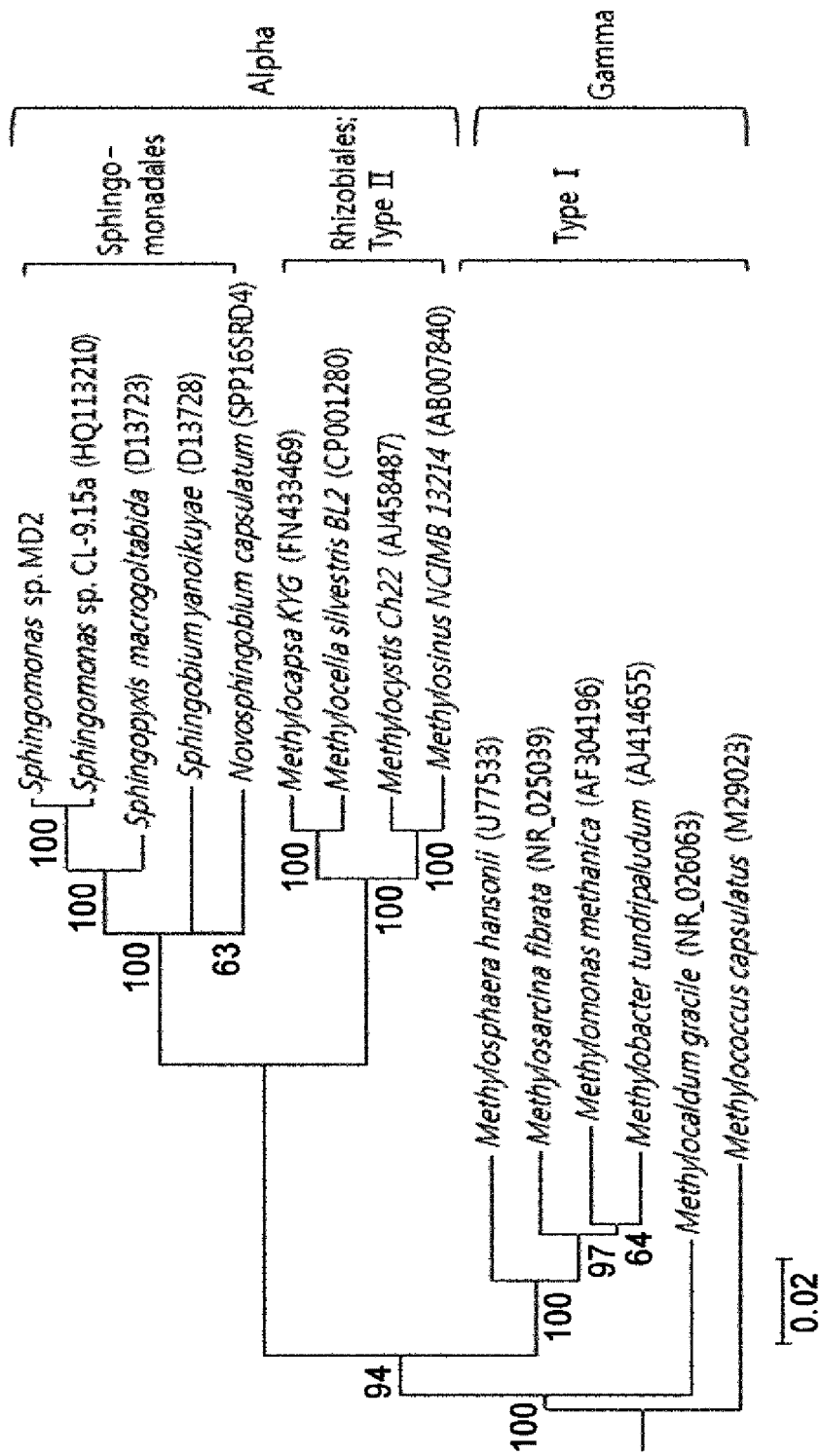
FIG. 1 shows a phylogenetic tree of *Sphingomonas* sp. MD2.

As a result, the strain MD2 capable of decomposing methane and dimethyl sulfide at the same time was isolated, and the result of 16S rDNA gene fragment analysis showed that it belongs to the genus *Sphingomonas*. The sequencing results (SEQ ID NO. 3) of the MD2 strain correspond to Table 1, and a phylogenetic tree showing strains similar to the MD2 strain is shown in FIG. 1.

TABLE 1

```
GGCATGCCTACACATGCAGTCGAACGAGATCCTTNCGGATNCTAGTGGCGCACGGGTGCGTAA

CGCGTGGGAATCCTGCCCTTTGGGTACGGAATAACTCAGTAGAAATTTGTGCTAATACCGTAT

ATGTCTTCGGACCAAAGATTTATCGCCCAAGGATGAGCCCGCGTAGGATTAGCTAGTTGGTGA

GGTAAAAGCTCACCAAGGCGACGATCCTTAGCTGGTCTGAGAGGATGATCAGCCACACTGGGA

CTGAGACACGGCCCAGACTCCTACGGGAGGCAGCAGTGGGGAATATTGGACAATGGGCGAAAG

CCTGATCCAGCAATGCCGCGTGAGTGATGAAGGCCCTAGGGTTGTAAAGCTCTTTTACCCGGG

ATGATAATGACAGTACCGGGAGAATAAGCTCCGGCTAACTTCGTGCCAGCAGCCGCGGTAATA

CGAGGGGAGCTAGCGTTGTTCGGAATTACTGGGCGTAAAGCGCGCGTAGGCGGTTTTTTAAGT

CAGAGGTGAAAGCCCGGGGCTCAACCCCGGAATAGCCTTTGAAACTGGAAAACTAGAATCTTG
```

TABLE 1-continued

```
GAGAGGTCAGTGGAATTCCGAGTGTAGAGGTGAAATTCGTAGATATTCGGAAGAACACCAGTG

GCGAAGGCGACTGACTGGACAAGTATTGACGCTGAGGTGCGAAAGCGTGGGGAGCAAACAGGA

TTAGATACCCTGGTAGTCCACGCCGTAAACGATGATAACTAGCTGTCCGGGCTCATAGAGCTT

GGGTGGCGCAGCTAACGCATTAAGTTATCCGCCTGGGGAGTACGGTCGCAAGATTAAAACTCA

AAGGAATTGACGGGGGCCTGCACAAGCGGTGGAGCATGTGGGTTTAATTCGAAGCAACGCGCA

GAACCTACCAGCGTTTGACATCCTGATCGCGGTTACCAGAGATGGTTTCCTTCAGTTCGGCTG

GATCAGTGACAGGTGCTGCATGGCTGTCGTCAGCTCGTGTCGTGAGATGTTGGGTTAAGTCCC

GCAACGAGCGCAACCCTCATCCCTAGTTGCCATCATTAAGTTGGGCACTCTAAGGAAACTGCC

GGTGATAAGCCGGAGGAAGGTGGGGATGACGTCAAGTCCTCATGGCCCTTACGCGCTGGGCTA

CACACGTGCTACAATGGCGGTGACAGTGGGCAGCAACCTCGCGAGAGGTAGCTAATCTCCAAA

AGCCGTCTCAGTTCGGATTGTTCTCTGCAACTCGAGAGCATGAAGGCGGAATCGCTAGTAATC

GCGGATCAGCATGCCGCGGTGAATACGTTCCCAGGCCTTGTACACACCGCCCGTCACACCATG

GGAGTTGGTTTCACCCGAAGGCAGTGCTCTAACCCGCAAGGGAGGAAGCTGACCACG
```

The results of phylogenetic analysis showed that the *Sphingomonas* sp. MD2 belongs to the class Alphaproteobacteria, the Family Sphingomonadales, in which any methane-oxidizing capability has not been identified yet, and that it has the highest similarity with the genus *Sphingomonas*. This *Sphingomonas* sp. MD2 is phylogenetically distinguished from the known methane-oxidizing bacteria belonging to the class Alphaproteobacteria, the family Rhizobiales, or the class Gammaproteobacteria (FIG. 1). These results indicate that the *Sphingomonas* sp. MD2 strain is a novel methane-oxidizing strain. The MD2 strain was deposited at the Biological Resource Center, Korea Research Institute of Bioscience and Biotechnology on Jan. 6, 2011 (accession number KCTC 11845BP).

EXAMPLE 3

Comparison of Growth Rate Between the *Sphingomonas* sp. MD2 Strain of the Present Invention and the Known Methane-Oxidizing Bacteria The growth rate between the known methane-oxidizing bacteria and the MD2 strain of the present invention was compared by way of the following method. As the known methane-oxidizing bacteria, *Methylocystis* sp. M6 (KCTC 11519BP) belonging to the type II methanotroph was used for the experiment. The *Methylocystis* sp. M6 strain grows only by utilizing methane or methanol having one carbon atom. Thus, the M6 strain was inoculated in a 2 L-fermentor containing 1 L of NMS medium at an initial absorbance (600 nm) of 0.109±0.0002, and then cultured at 30° C. with shaking at 180 rpm while continuously injecting air containing 20% (v/v) methane.

The MD2 strain of the present invention is a heterotrophic bacterium that can grow in the medium containing complex substrates. Thus, the MD2 strain was inoculated in Bacto™ Triptic Soy Broth (Becton, Dickinson and Company, USA) at an initial absorbance (600 nm) of 0.06±0.0007, followed by culturing at 30° C. with shaking at 180 rpm.

During cultivation of the two types of strains, 1 ml of the culture broth was collected periodically, and the absorbance of the culture broth was measured at 600 nm and shown in FIG. 2.

As shown in FIG. 2, when the *Methylocystis* sp. M6 strain was cultured for 4 days, the absorbance at 600 nm was increased to approximately 1. In contrast, the MD2 strain of the present invention is a heterotrophic bacterium utilizing complex substrates as a carbon source and 2 days after cultivation its absorbance at 600 nm, measured after dilution, was increased to approximately 18. These results showed that the MD2 strain of the present invention can be easily mass-cultured by using inexpensive substrates such as organic waste in a short period of time, and thus has viability for being applied to various industries, whereas the conventional methane-oxidizing bacterium has very low growth rate and the risk of combustion becomes a factor, and additionally its viability for mass-production in industrial application is also limited because of the utilization of expensive methane gas as a substrate.

EXAMPLE 4

Evaluation of Methane and Odor-Decomposing Ability of *Sphingomonas* sp. MD2 of the Present Invention 4-1. Evaluation of Methane and DMS-Decomposing Ability In order to evaluate methane and odor-decomposing ability of the *Sphingomonas* sp. MD2 strain of the present invention, pre-culture of the MD2 strain was performed as follows. 20 ml of NMS medium was added to 600 ml-serum bottles, and the isolated methane-oxidizing pure strain was inoculated, and the bottles were sealed with a butyl rubber septum. Methane was injected into the sealed serum bottle to a final concentration of 5% (v/v), 2 µl of the DMS solution was also injected, followed by incubation at 30° C. with shaking at 200 rpm. The methane and DMS concentrations were measured every other day, and when the concentrations dropped below a detection limit methane and DMS were re-injected at the same concentration. After the re-injection of methane and DMS had occurred three times, when the oxidation rates of methane and DMS decreased, the rubber septum was opened, and only the strain was recovered by centrifugation at 8000 rpm for 10 minutes. The recovered strain was suspended in 40 ml of NMS, and then each 20 ml thereof was aliquoted to 600 ml-serum bottles, and subcultured using a total of 2 serum bottles. After passaging a total of three times in the same way, a total of 8 serum bottles were prepared.

The strains pre-cultured in a total of 8 serum bottles were collected Info one bottle, and then centrifuged at 8000 rpm for 10 minutes to recover only the strain. The recovered strain was suspended in 50 ml of NMS, and then each 4 ml thereof was aliquoted in 120 ml-serum bottles. Each bottle was sealed with a butyl rubber septum, and then methane and DMS were added thereto according to three conditions (injection of methane only, injection of methane together with DMS, and injection of DMS only). Methane was injected to a final concentration of 5% (v/v), and 2 of the DMS solution was also injected. Each serum bottle was incubated at 30° C. with shaking at 200 rpm, and 0.3 ml of the gases in the headspace of each serum bottle was sampled every three hours using a gas-tight syringe and analyzed via gas chromatography to measure the methane and DMS residual concentrations. The specific oxidation rates were calculated from the slope of the graph of methane and DMS concentrations against time. All experiments were repeated three times, and the results are shown in FIG. 3.

As shown in FIG. 3, when only methane was injected, the MD2 strain could decompose methane (FIG. 3a), and when both methane and DMS were injected, it could decompose methane (FIG. 3b) and also DMS within 2 days, completely (FIG. 3c). However, when only DMS was injected without methane, the decomposition rate of DMS was very low (FIG. 3d). When only methane was injected, the methane decomposition rate of the MD2 strain was 2634±148 μmole·g-dry cell weight$^{-1}$h$^{-1}$. When both methane and DMS were injected, the methane and DMS decomposition rates of the MD2 strain were 2320±96 μmole·g-dry cell weight$^{-1}$h$^{-1}$ and 50±16 μmole·g-dry cell weight$^{-1}$h$^{-1}$, respectively. These results indicate that the *Sphingomonas* sp. MD2 strain of the present invention is a microorganism capable of decomposing methane and DMS concurrently.

4-2. Evaluation of Methane, MT and Hydrogen Sulfide-Decomposing Ability

In order to examine whether the MD2 strain is able to decompose the representative odor-producing sulfur compounds, MT and hydrogen sulfide other than DMS, methane gas was injected to a final concentration of 5% (v/v) into 120 ml-serum bottles (containing 4 ml of MD2 strain-inoculated NMS medium) prepared by an identical manner as in the above method. MT gas (99%, Sigma Aidrich, USA) was injected thereto to a final concentration of 1000 ppm, or hydrogen sulfide gas (99%, Seoul special gas, Korea) was injected thereto to a final concentration of 2000 ppm, and the serum bottles were incubated at 30° C. with shaking at 200 rpm. While conducting incubation with shaking, 0.3 ml of the gases in the headspace of each serum bottle was sampled once a day using a gastight syringe, and the methane concentration was analyzed via gas chromatography equipped with a flame ionization detector. In addition, 0.06 ml of the gas in the serum bottle was sampled, and the MT or hydrogen sulfide concentration was analyzed via gas chromatography equipped with a flame Ionization detector. The results are shown in Table 2.

TABLE 2

| Condition | Methane + MT mixed | | Methane + Hydrogen sulfide mixed | |
|---|---|---|---|---|
| Decomposition ability | Methane | MT | Methane | Hydrogen sulfide |
| Decomposition State | decomposed | decomposed | decomposed | decomposed |
| Methane decomposition rate (relative to 100 being the decomposition rate under the injection of only methane) | 85 | — | 90 | — |

As shown in Table 2, it was found that the MD2 strain is able to decompose methane given the coexistence of odor-producing compounds such as MT and hydrogen sulfide. When compared to the methane decomposition rate of the MD2 strain under the injection of only methane, the methane decomposition rates under the coexistence of MT and hydrogen sulfide were 85% and 90%, respectively, indicating that the MD2 strain is rarely affected thereby, and is able to decompose methane under the coexistence of MT and hydrogen sulfide (Table 2).

The results of FIG. 3 and Table 2 showed that the *Sphingomonas* sp. MD2 strain of the present invention is a strain having an ability to decompose the representative odor-producing compounds, DMS, MT, and hydrogen sulfide as well as methane.

EXAMPLE 5

Preparation of Microorganism Formulation of *Sphingomonas* sp. MD2 Strain of the Present Invention and Evaluation of the Number of Viable Cells The microorganism formulations of the MD2 strain of the present invention were prepared as follows. The culture broth of the MD2 strain that was mass-cultured in Bacto™ Triptic Soy Broth (Sectors, Dickinson and Company, USA) at 30° C. and 180 rpm was absorbed by defatted rice bran without pretreatment, and then dried by 45° C. hot air to prepare a defatted rice bran microorganism formulation. In addition, the MD2 strain culture broth was centrifuged (8,000 rpm, 10 minutes), and the cell pellet was only recovered, and suspended in an equal volume of distilled water, and 10 g/L of sucrose was added, and mixed well. The MD2 cell mixture was completely absorbed into bentonite or starch, and then dried by hot air at 45° C. When bentonite was used as an absorbent, 0.4 L of the MD2 cell suspension was absorbed into 1 kg of bentonite (bentonite microorganism formulation). When starch was used, 1 L of the cell suspension was absorbed into 1 kg of starch to prepare a microorganism formulation (starch microorganism formulation).

Each microorganism formulation prepared was put in a bottle, and the survival rate of the strain was examined while stored in the dark. Each 1 g of the formulations was suspended in 9 ml of 0.9% NaCl solution, and then serially diluted 1/10-fold in distilled water. The diluted solutions were plated on Bacto™ Triptic Soy-agar plates prepared by addition of 15 g/L agar to Bacto™ Triptic Soy Broth, and then incubated at 30° C. The number of colonies formed on the plate was counted, and shown in Table 3.

TABLE 3

| Type of microorganism formulation | Changes in the number of MD2 viable cells according to storage time (cfu/g-dry weight of microorganism formulation) | | | |
|---|---|---|---|---|
| | Day 1 | 1 month | 3 months | 6 months |
| Defatted rice bran microorganism formulation | $3.5 \times 10^8$ | $2.8 \times 10^8$ | $1.7 \times 10^8$ | $8.5 \times 10^7$ |
| Bentonite microorganism formulation | $2.8 \times 10^9$ | $1.4 \times 10^9$ | $9.8 \times 10^8$ | $7.1 \times 10^8$ |
| Starch microorganism formulation | $3.2 \times 10^9$ | $1.8 \times 10^9$ | $8.6 \times 10^8$ | $2.3 \times 10^8$ |

As shown in Table 3, three types of the MD2 microorganism formulations did not show a great reduction in the number of viable cells until stored for 6 months (Table 3). These results indicate that the microorganism formulation prepared by using the MD2 strain of the present invention is excellent in terms of stability.

EXAMPLE 6

Figure 4:
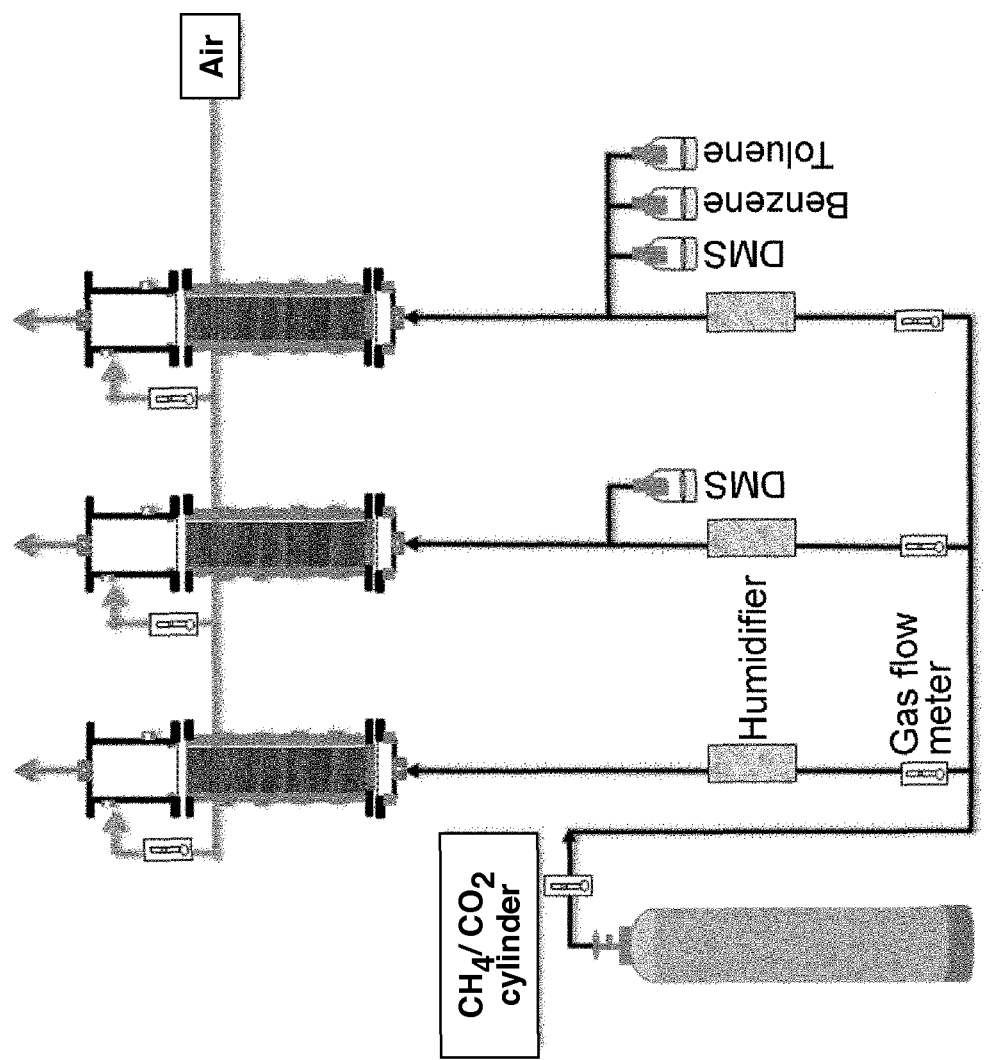
FIG. 4 is a diagram showing the biocover device used for evaluating the performance of the biocover using the *Sphingomonas* sp. MD2 strain.

Evaluation of Performance of Biocover Using *Sphingomonas* sp. MD2 Strain of the Present Invention 6-1. Experimental Method In order to demonstrate the methane and odor-removal characteristics of the MD2 strain-inoculated functional biocover, a lab-scale biocover was manufactured. The lab-scale biocover was manufactured using an acrylic column and a detailed diagram of the device is shown in FIG. 4.

The biocover consists of a charging unit having a diameter of 8 cm and a height of 50 cm, a ventilating unit having a diameter of 8 cm and a height of 15 cm, and a gas supply unit having a diameter of 8 cm and a height of 5 cm.

200 ml of the MD2 strain pre-cultured in a Bacto™ triptic soy medium was added to 2.2 kg of soil mixture prepared by mixing the soils from the Gapyeong-gun landfill, activated carbon, earthworm casting, and decomposed granite soil at a weight ratio of 4:2:1:1, mixed by hand, and put in the charging unit of each biocover.

The gas supply unit at the bottom of the biocover was packed with orchid stones (diameter of 5-10 mm) for uniform supply of gas to the charging unit of the biocover. Methane/carbon dioxide (40:60% (v/v), Seoul Special Gas, Korea) gas was supplied at a flow rate of 5 ml/minute to the biocover after the gas was passed through a humidifier in order to prevent drying of the biocover.

Methane/carbon dioxide gas was only supplied to 'biocover 1'. A gas mixture of methane/carbon dioxide/DMS was supplied to 'biocover 2' as follows: 200 ml of 1:9 (v/v) mixture of DMS solution (99%, Junsei, Japan) and water, and 50 ml of cooking oil were put in a 1 L-container, and the container was connected to a methane/carbon dioxide gas tube, and vaporized DMS gas and the gas mixture of methane/carbon dioxide/DMS were supplied to biocover 2.

A gas mixture of methane/carbon dioxide/DMS/benzene/toluene was supplied to 'biocover 3' as follows: 200 ml of 1:2 (v/v) mixture of benzene solution (99.7%, Kanto chemical, Japan) and cooking oil, and 200 ml of 1:2 (v/v) mixture of toluene solution (100%, J C Baker, USA) and cooking oil were put in 0.5 L-containers, and the DMS solution was put in a 1 L-container. The containers were connected to the methane/carbon dioxide gas tube, and vaporized DMS, benzene and toluene gas and the gas mixture of methane/carbon dioxide/DMS were supplied to biocover 3. The injection concentrations of methane, DMS, benzene, and toluene were 40%, 500-2,900 ppm, 300-800 ppm, and 50-150 ppm, respectively.

Air was continuously supplied to the ventilating unit at the top of the biocover at a flow rate of 100 ml/min for imitating the atmosphere contact with the landfill soils. The biocover was operated for 20 days at room temperature (20±5° C.). During operation of the biocover, 300 _l of gas was sampled from the inlet and outlet sampling ports of the biocover once every day or every other day using a 500-_l gas-tight syringe, and analyzed via gas chromatography equipped with a flame ionization detector to measure each concentration of gases. The removal ratio was determined by a difference in the concentration between the inlet and outlet.

6-2. Results

The methane and odor-decomposition results by the *Sphingomonas* sp. MD2 strain-inoculated biocover, obtained according to Example 6-1, are shown in FIGS. 5 to 10.

Figure 5A:
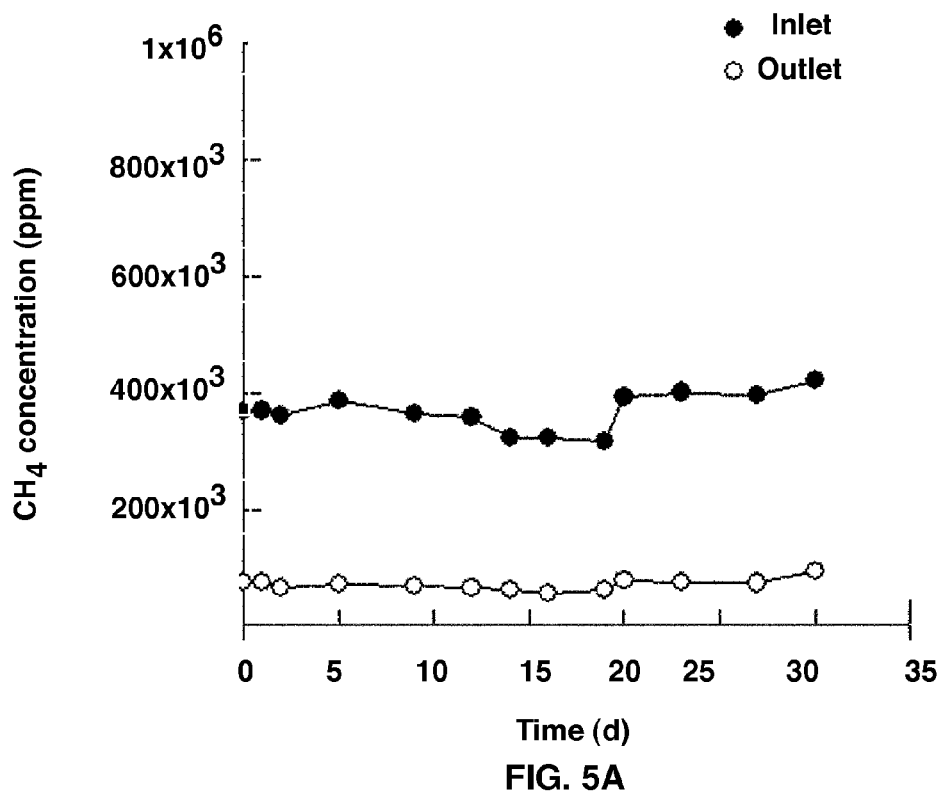
FIGS. 5A-5B are graphs showing inlet and outlet concentrations (FIG. 5A) of methane in biocover 1 and efficiency of its removal (FIG. 5B)
Figure 5B:
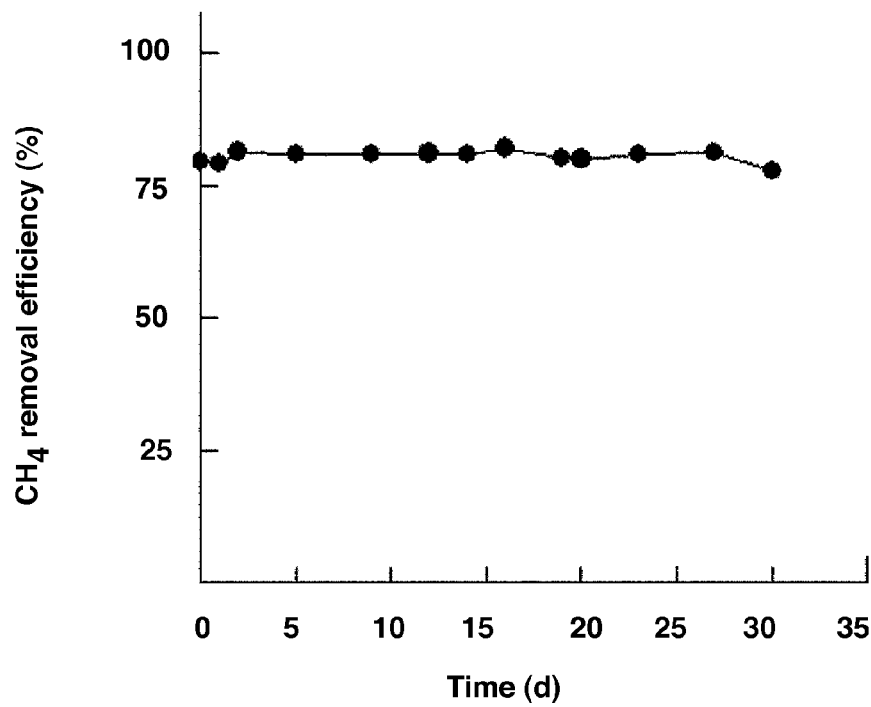
Figure 6A:
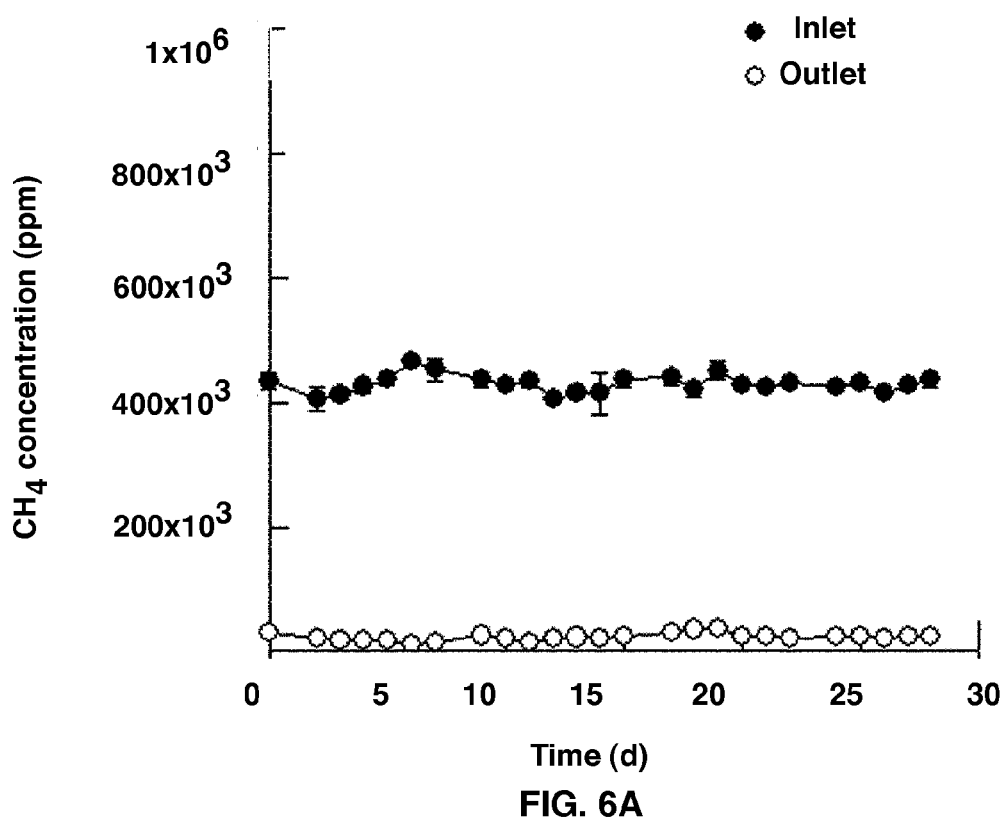
FIGS. 6A-6B are graphs showing inlet and outlet concentrations (FIG. 6A) of methane in biocover 2 and efficiency of its removal (FIG. 6B)
Figure 6B:
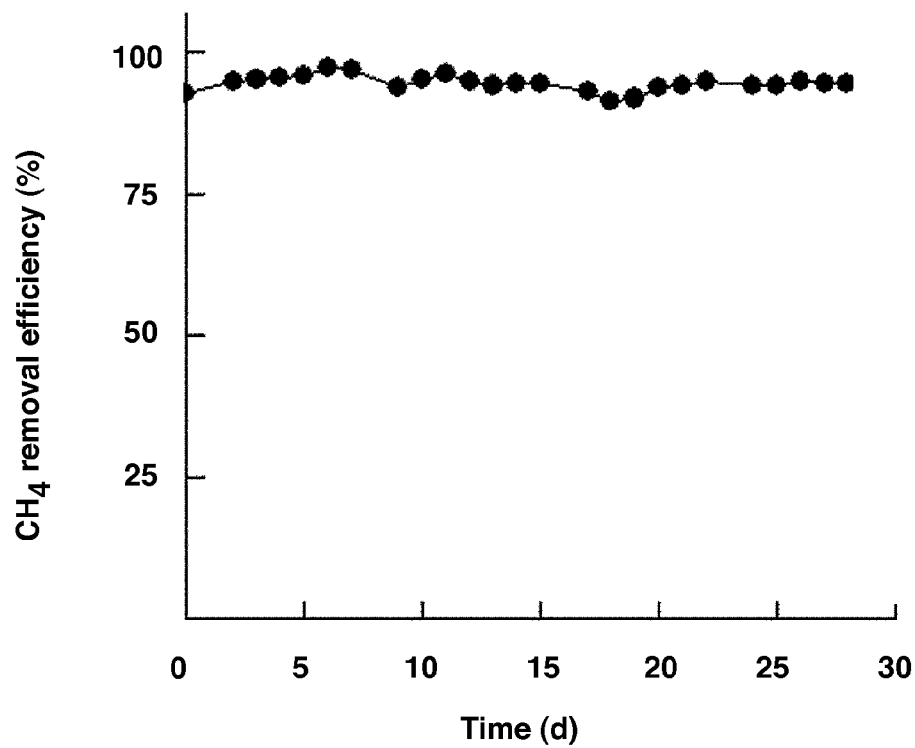

In biocover 1 supplied with methane only, when methane of 400,000 ppm was supplied thereto, the methane removal efficiency was 78-81%, and the average was approximately 80%, indicating consistent removal efficiency (FIG. 5).

Figure 7A:
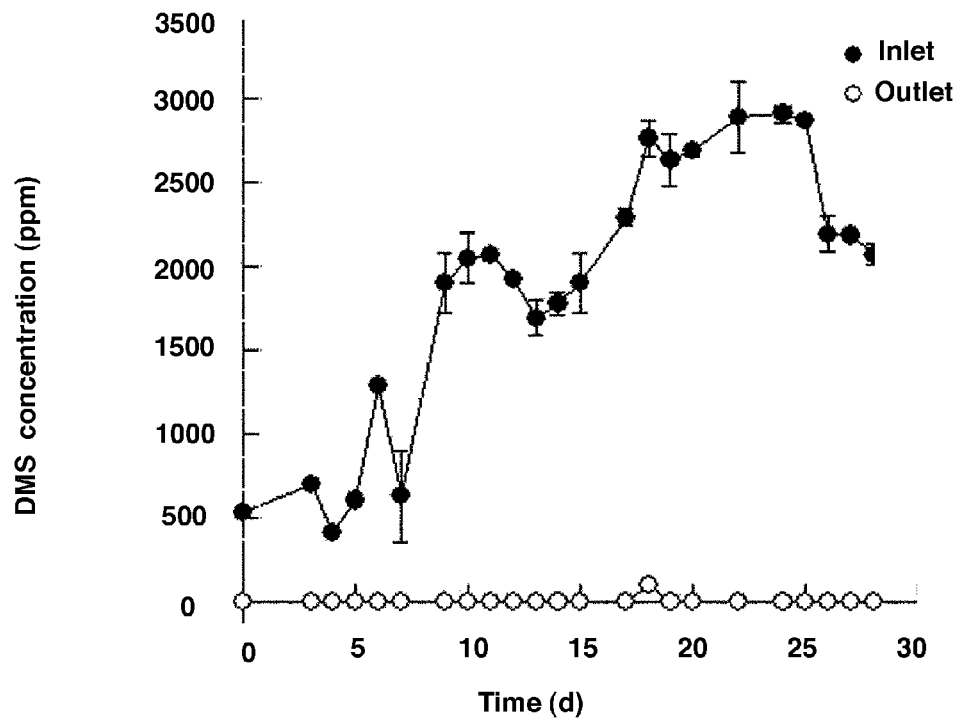
FIGS. 7A-7B are graphs showing inlet and outlet concentrations (FIG. 7A) of DMS in biocover 2 and its efficiency of removal (FIG. 7B)
Figure 7B:
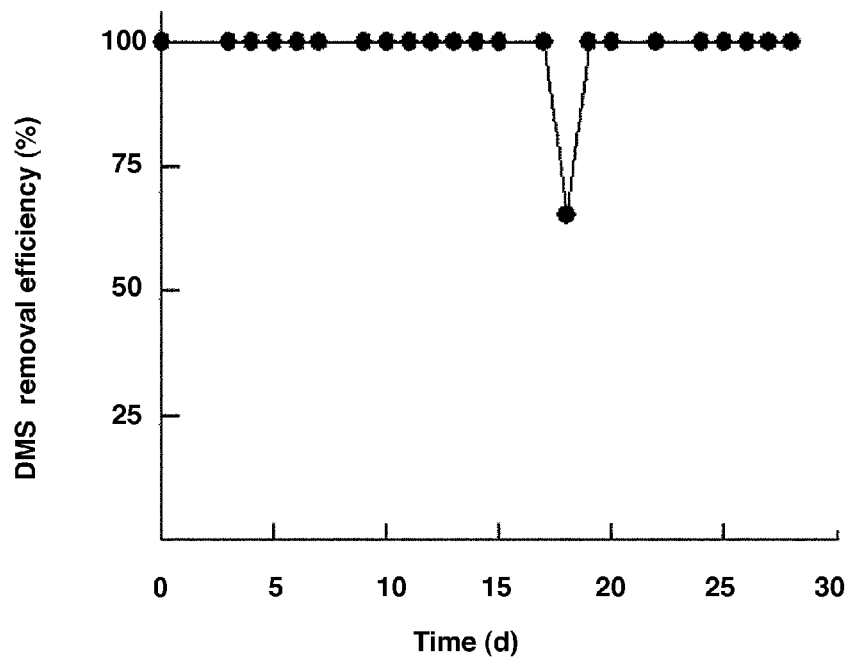
Figure 8A:
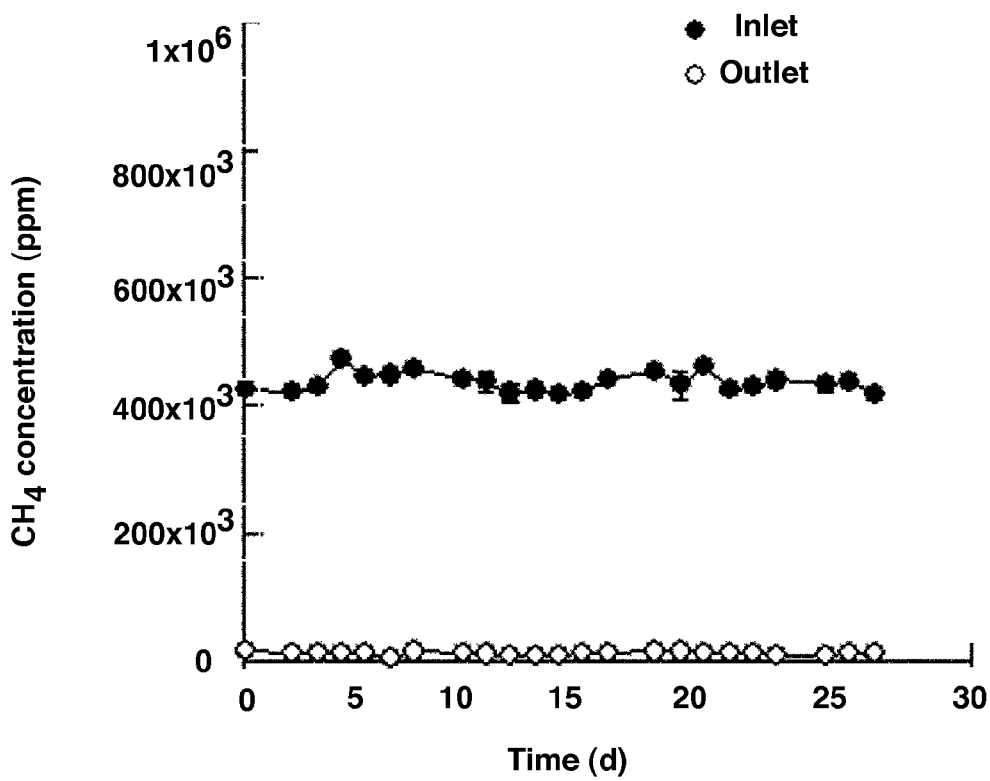
FIGS. 8A-8B are graphs showing inlet and outlet concentrations (FIG. 8A) of methane in biocover 3 and its efficiency of removal (FIG. 8B)
Figure 8B:
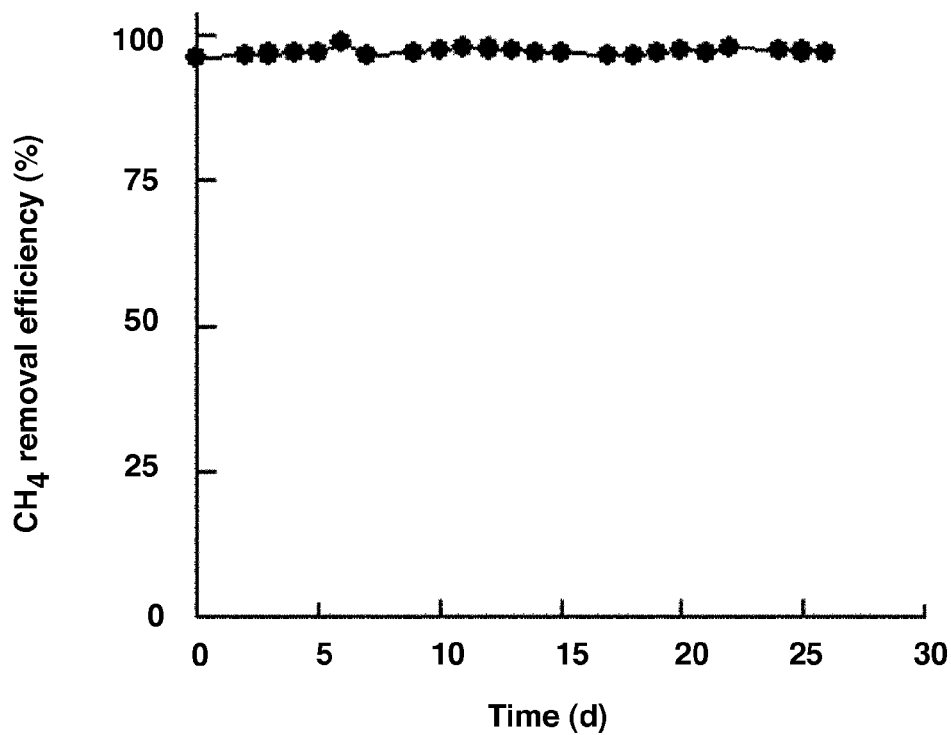

In biocover 2 supplied with both methane and DMS, when methane of 400,000 ppm was supplied thereto, the high methane removal efficiency of 91-97% was maintained (FIG. 8). DMS was almost completely removed at the beginning of the operation. Even though the DMS injection concentration was gradually increased to 500-2,900 ppm, 100% of DMS removal efficiency was stably maintained (FIG. 7).

Figure 9A:
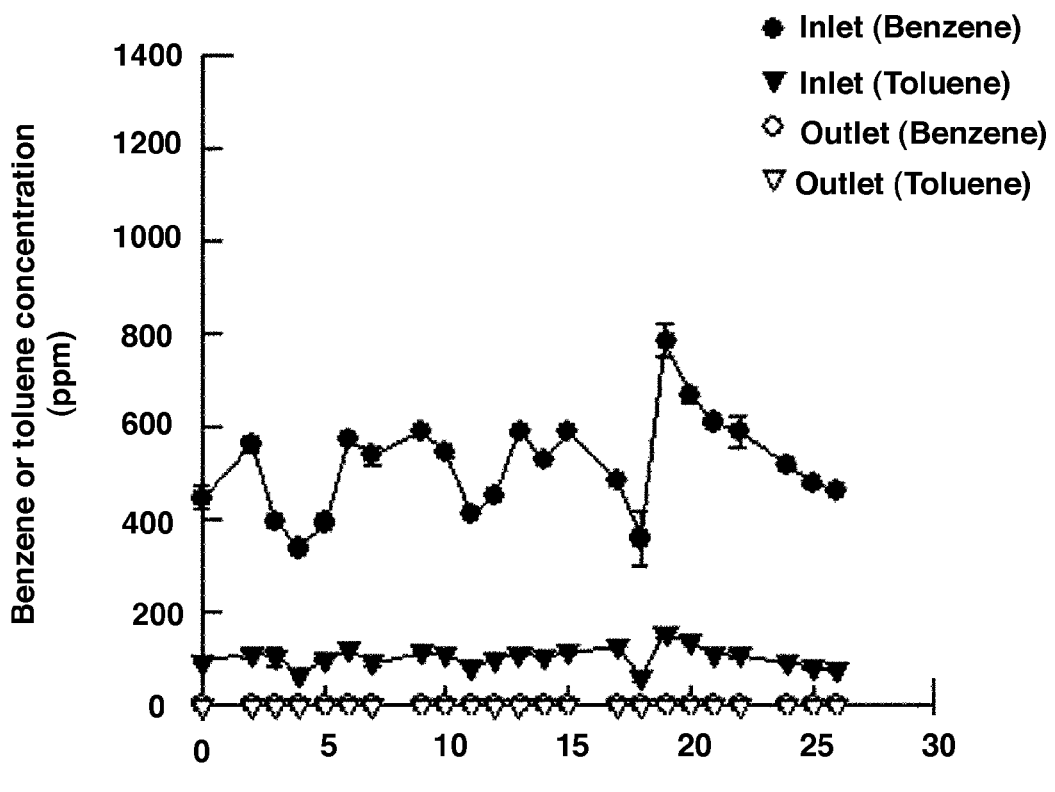
FIGS. 9A-9B are graphs showing inlet and outlet concentrations (FIG. 9A) of benzene or toluene in biocover 3 and their efficiency of removal (FIG. 9B)
Figure 9B:
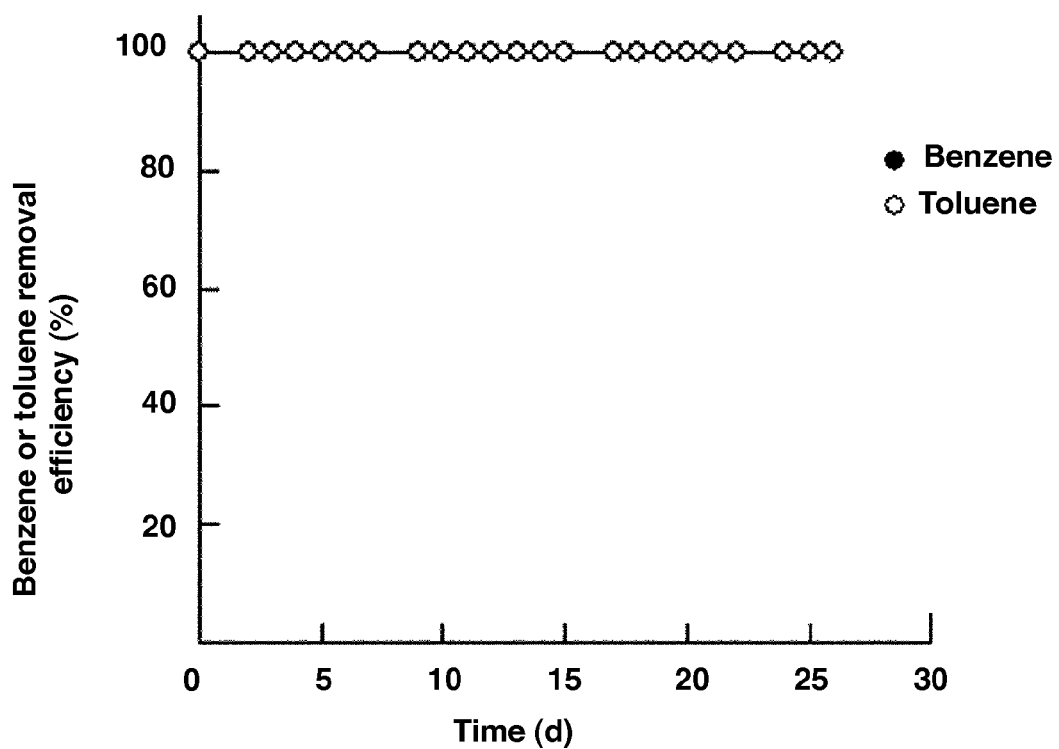
Figure 10A:
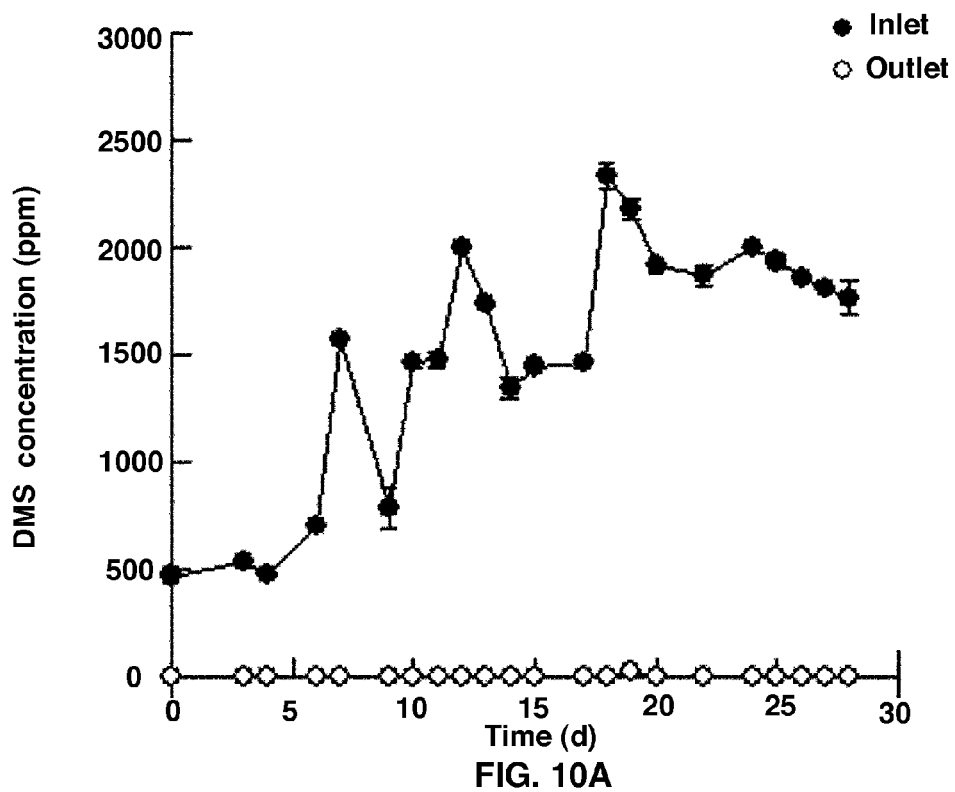
FIGS. 10A-10B are graphs showing inlet and outlet concentrations (FIG. 10A) of DMS in biocover 3 and its efficiency of removal (FIG. 10B)
Figure 10B:
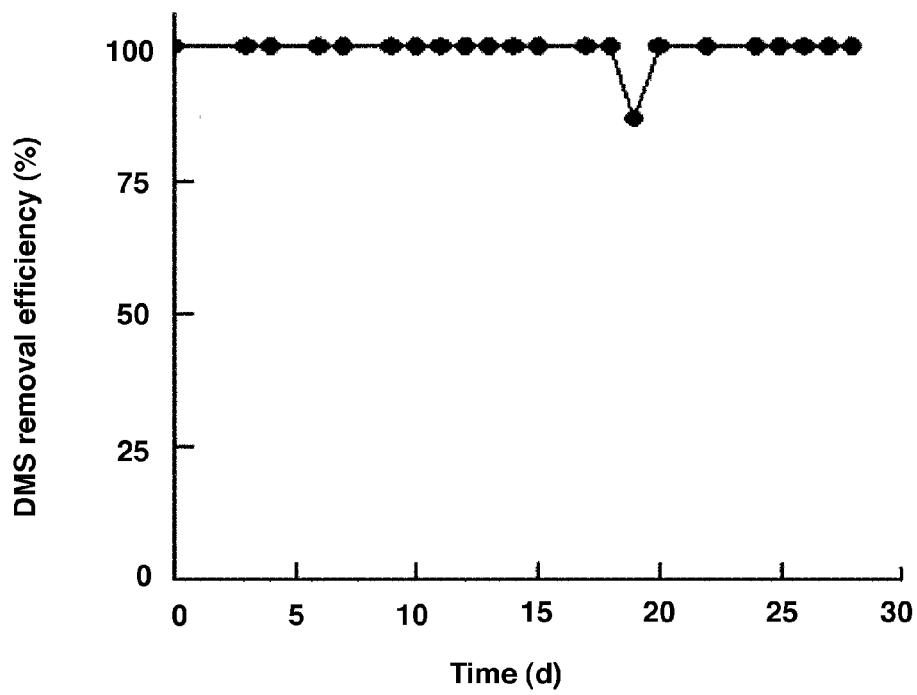

In biocover 3 supplied with all of methane, DMS, benzene, and toluene, when methane of 400,000 ppm was supplied thereto, the high methane removal efficiency of 96-98% was maintained (FIG. 8). DMS, benzene, and toluene were almost completely removed at the beginning of the operation. Even though the DMS injection concentration was gradually increased to 500-2,300 ppm and the benzene and toluene injection concentrations were gradually increased to 300-800 ppm and 50-150 ppm, respectively, 100% of the odor-producing compounds were consistently removed (FIGS. 9 and 10).

These results indicate that the *Sphingomonas* sp. MD2 strain-inoculated biocover is able to effectively remove methane and odor-producing compounds such as dimethyl sulfide/benzene/toluene at the same time, and its performance was consistently maintained.

EXAMPLE 7

Figure 11:
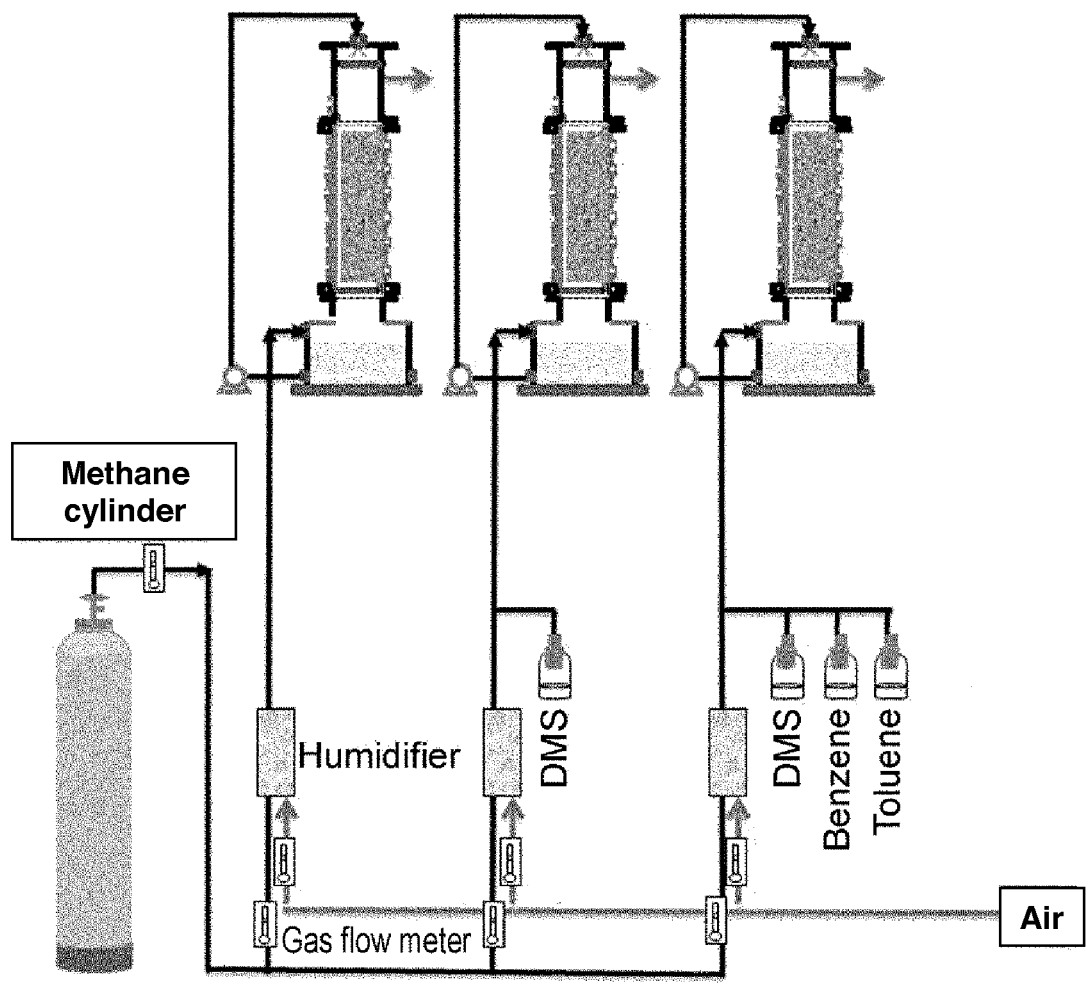
FIG. 11 is a diagram showing the biofilter device for evaluating the performance of the biofilter using the *Sphingomonas* sp. MD2 strain.

Evaluation of Performance of Biofilter Using *Sphingomonas* sp. MD2 Strain of the Present Invention 7-1. Experimental Method In order to demonstrate methane and odor-removal characteristics of the MD2 strain-inoculated functional biofilter, a lab-scale biofilter was manufactured. The lab-scale biofilter was manufactured using an acrylic column and a detailed diagram of the device is shown in FIG. 11. The device consists of a biofilter having a diameter of 8 cm and a height of 100 cm, a drain storage tank having a diameter of 20 cm and a height of 15 cm, and a liquid spray device. The porous net is installed at the bottom of the biofilter for uniform supply of gas to the charging unit, and pea gravel and activated carbon were packed as supports. In order to prevent drying of the supports in the biofilter and continuously supply inorganic salts to the microorganism, the inorganic salt medium NMS was added to the drain storage tank. This solution was sprayed from the top portion to the bottom portion of the biofilter using a circulation pump four times a day for 1 minute. The inorganic salt medium in the drain storage tank was replaced once every seven days.

The gas mixture of methane/air was supplied to 'biofilter 1'. The pure methane (99%, Seoul special gas, Korea) gas and air were supplied to the biofilter after the gas was passed through a humidifier in order to prevent drying of the biofilter. A gas mixture of methane/air/DMS was supplied to 'biofilter 2' as follows: 200 ml of 1:20 (v/v) mixture of DMS solution (99%, Junsei, Japan) and cooking oil were put in a 1 L-container, and the container was connected to compressed air, and forced vaporized DMS/air and methane gas were passed through the humidifier and then supplied to biofilter 2.

A gas mixture of methane/air/DMS/benzene/toluene was supplied to 'biofilter 3' as follows: 200 ml of 1:20 (v/v) mixture of benzene solution (99.7%, Kanto chemical, Japan) and cooking oil, 200 ml of 1:20 (v/v) mixture of toluene solution (100%, J C Baker, USA) and cooking oil, and 200 ml of 1:20 (v/v) mixture of DMS and cooking oil were put in 1 L-containers. Compressed air was connected to the 1 L-container in parallel, and forced vaporized DMS/benzene/toluene/air and methane gas were passed through the humidifier and then supplied to biofilter 3.

In this experiment, pea gravel (diameter of 5~10 mm, Japan) and activated carbon (diameter of 4~8 mm, Korea) were used as supports. The weight ratio of orchid stone and activated carbon was 1:10 (w/w), and each biofilter was packed with 2000 g of pea gravel and 200 g of activated carbon.

500 ml of MD2 strain pre-cultured in the Bacto™ Triptic Soy Broth and 500 ml of earthworm casting (NanJi Sewage Treatment Center, Korea) 10-fold diluted in NMS were inoculated in the drain storage tank, together with 1.5 L of NMS. In order to adsorb the bacteria to the supports, the solution was sprayed to the biofilters using a circulation pump four times a day for 2 minutes over 7 days.

'Biofilter 1' was operated under the conditions of a methane supply concentration of 1-6% and a retention time of 20 minutes (250 ml/min; 3 h$^{-1}$) for 20 days at room temperature (20±5° C.). 'Biofilter 2' was operated under the conditions of methane supply concentration of 1-6% and DMS supply concentration of 50-300 ppm and the retention time of 20 minutes (250 ml/min; 3 h$^{-1}$) for 20 days at room temperature (20±5° C.). 'Biofilter 3' was operated under the conditions of a methane supply concentration of 1-5%, DMS supply concentration of 50-300 ppm, and benzene and toluene supply concentration of 10-200 ppm and the retention time of 20 minutes (250 ml/min; 3 h$^{-1}$) for 20 days at room temperature (20±5° C.).

300 μl of gases were sampled from the inlet and outlet of the biofilter using a 500-_l gaslight syringe, and analyzed via gas chromatography equipped with a flame ionization detector to measure the concentrations of methane, DMS, benzene and toluene. The removal ratio of each gas was determined by a difference in the concentration between the inlet and outlet. In order to monitor the decomposition products of methane, DMS, benzene and toluene, the carbon dioxide concentration in the sampled gas was analyzed via gas chromatography equipped with a thermal conductivity detector, and the concentrations of MT and hydrogen sulfide were via gas chromatography equipped with a flame ionization detector. The DMSO and sulfate concentrations in the filtrates obtained by filtration (0.4 μm syringe filter) of the solution in the drain storage tank of each biofilter were analyzed via high performance liquid chromatography (HPLC) and ion chromatography (IC).

7-2. Results

The methane and odor-decomposition results by the *Sphingomonas* sp. MD2 strain-inoculated biofilter are shown in FIGS. 12 to 17 and Tables 4 and 5.

Figure 12A:
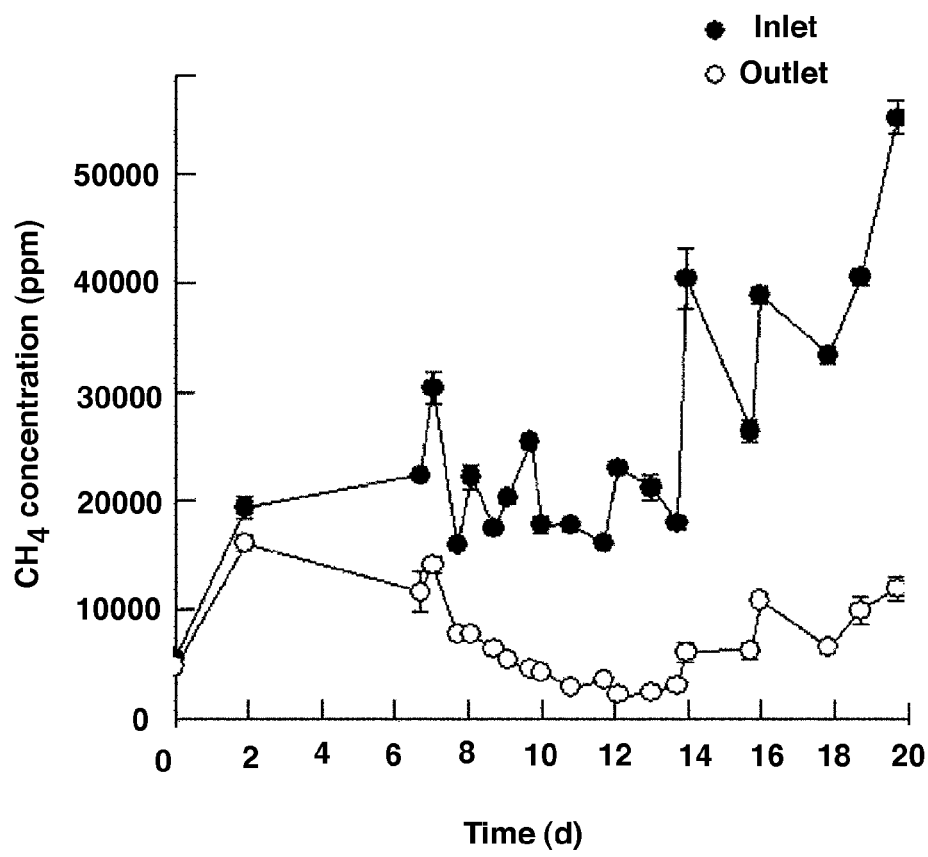
FIGS. 12A-12B are graphs showing inlet and outlet concentrations (FIG. 12A) of methane in biofilter 1 and its efficiency of removal (FIG. 12B)
Figure 12B:
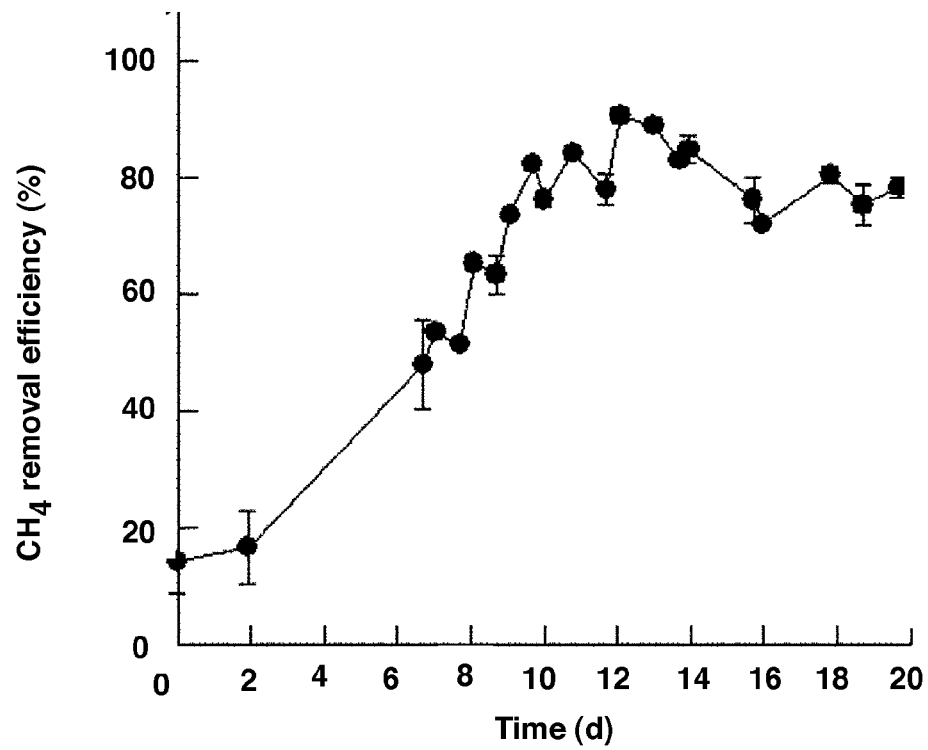

In biofilter 1 supplied with only methane, methane removal efficiency of less than 20% was observed at the beginning of the operation, but the efficiency increased over time and a methane removal efficiency of 90% or more was observed after 12 days. Even though the methane concentration at the inlet increased over time, average methane efficiency of 80% was stably maintained (FIG. 12).

Figure 13A:
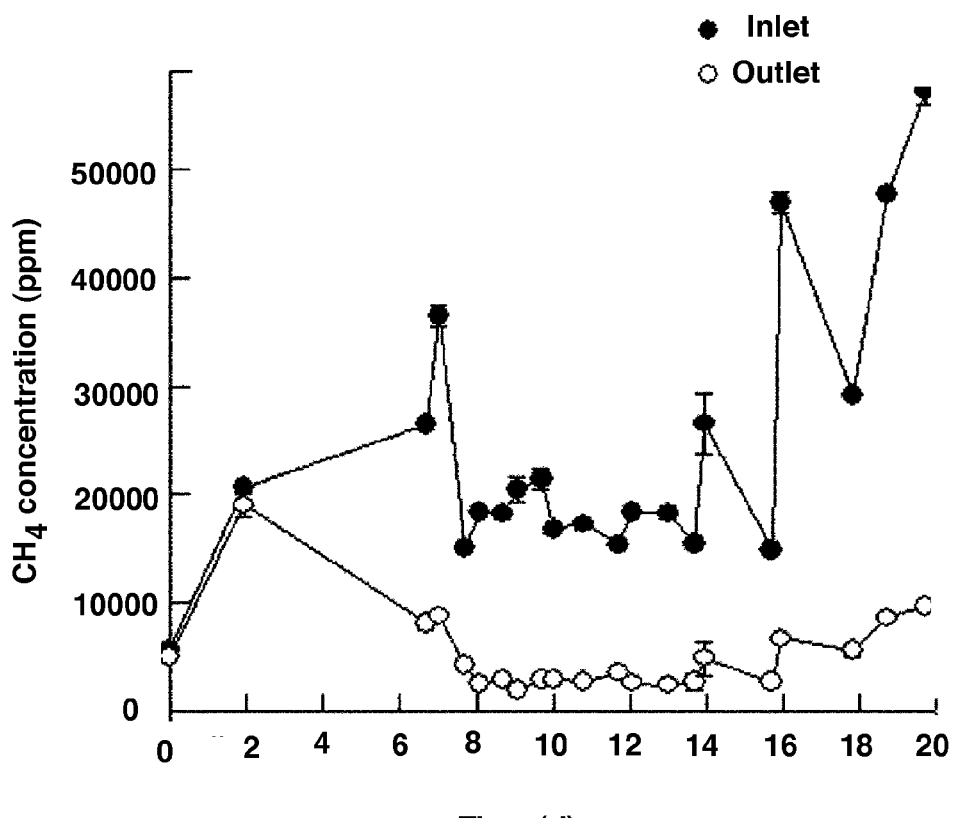
FIGS. 13A-13B are graphs showing inlet and outlet concentrations (FIG. 13A) of methane in biofilter 2 and its efficiency of removal (FIG. 13B)
Figure 13B:
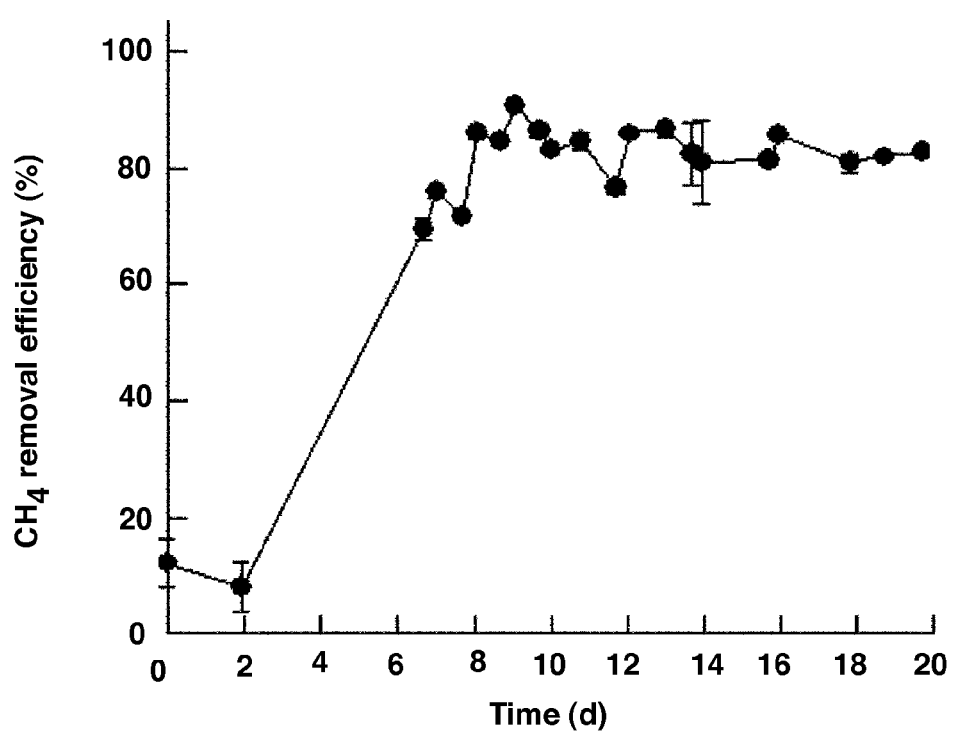
Figure 14A:
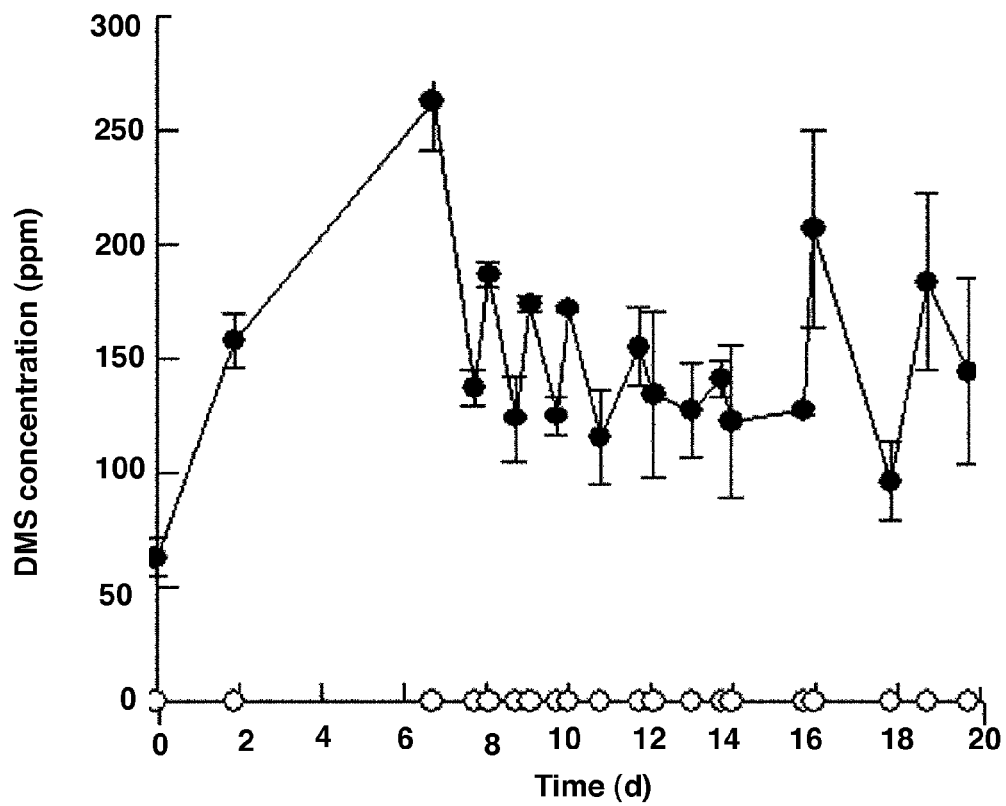
FIGS. 14A-14B are graphs showing inlet and outlet concentrations (FIG. 14A) of DMS in biofilter 2 and its efficiency of removal (FIG. 14B)
Figure 14B:
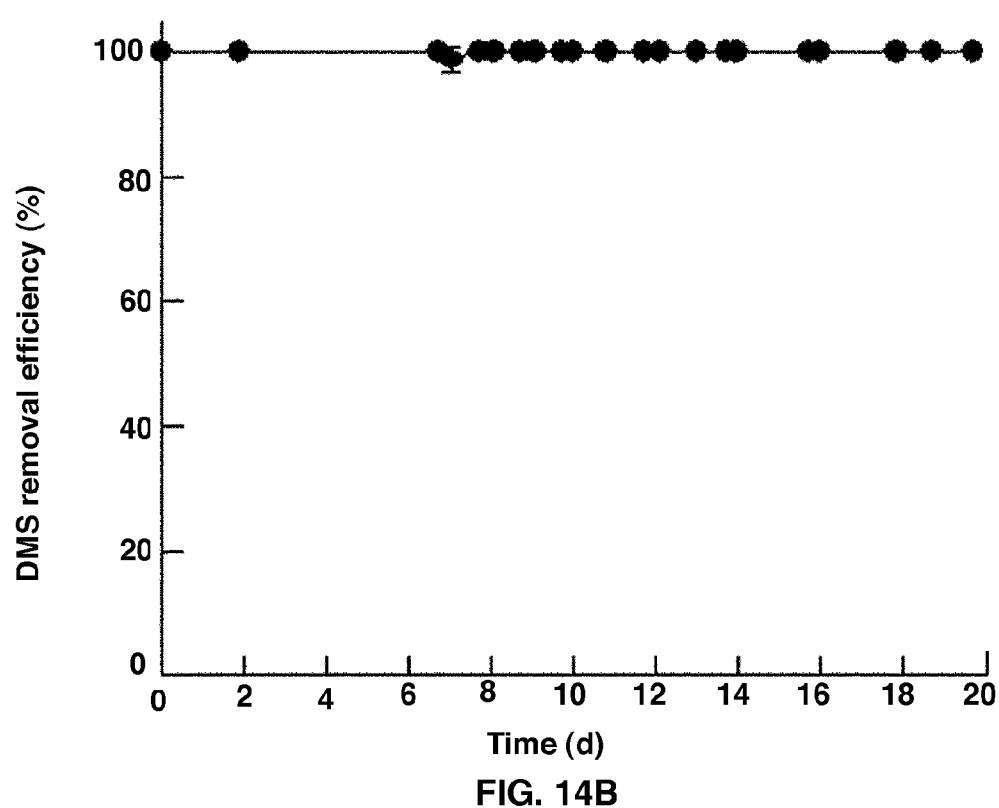

In biofilter 2 supplied with both methane and dimethyl sulfide, methane removal efficiency of less than 20% was observed at the beginning of the operation, but the efficiency increased over time and methane removal efficiency of 80% or more was observed after 8 days. Even though the methane concentration at the inlet increased over time, an average methane efficiency of 80% was stably maintained (FIG. 13). Dimethyl sulfide was completely removed at the beginning of the operation (FIG. 14).

Figure 15A:
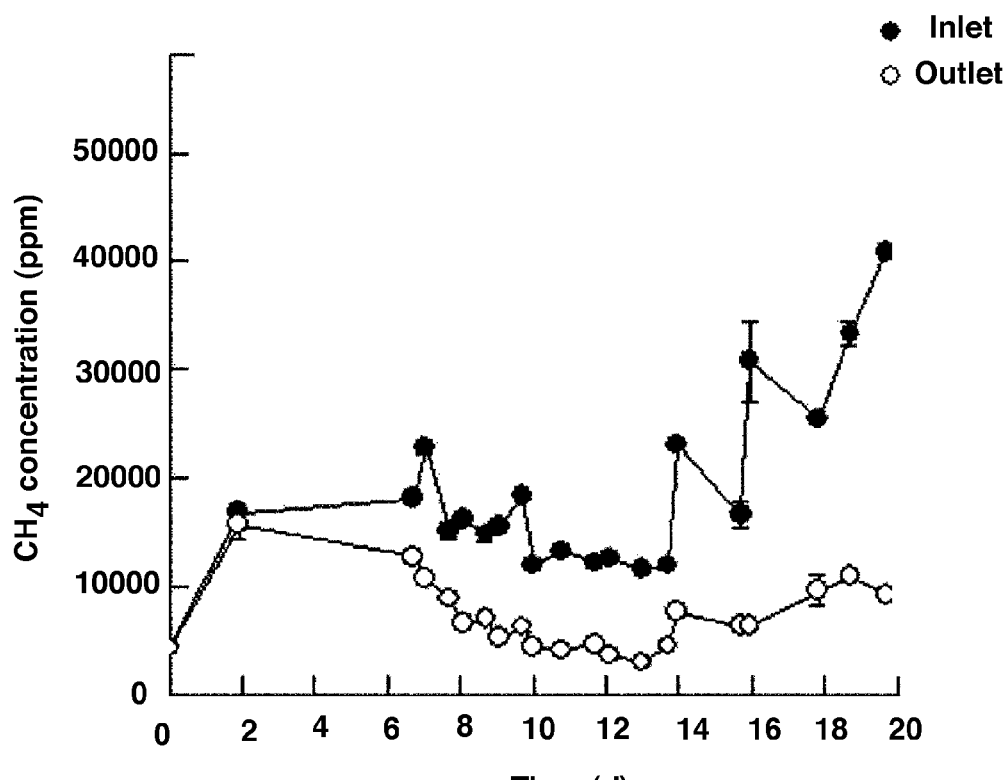
FIGS. 15A-15B are graphs showing inlet and outlet concentrations (FIG. 15A) of methane in biofilter 3 and its efficiency of removal (FIG. 15B)
Figure 15B:
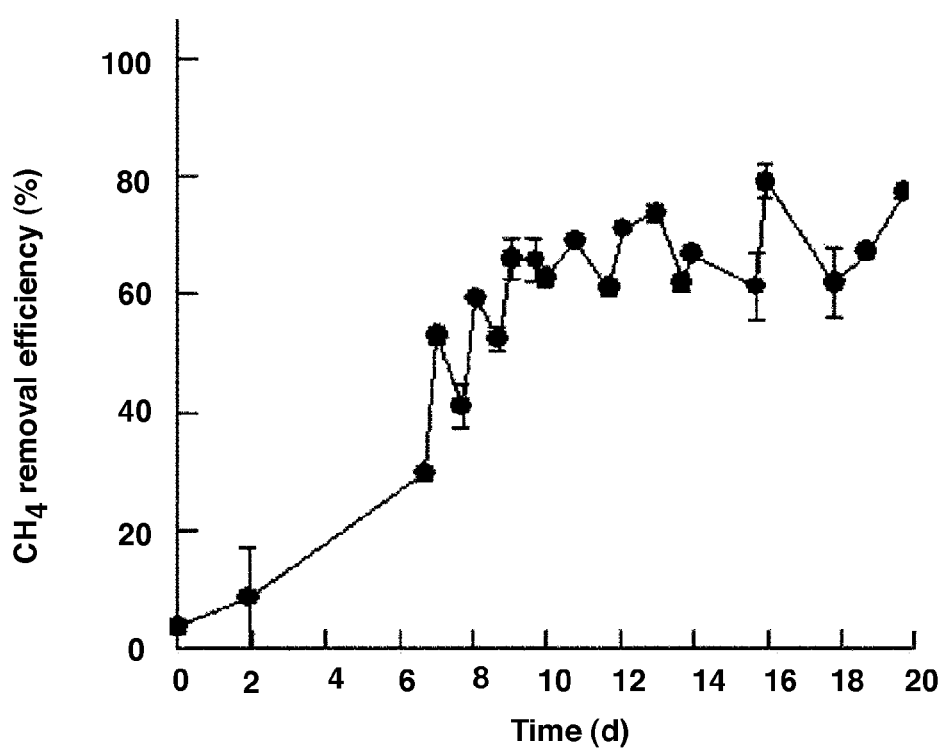
Figure 16A:
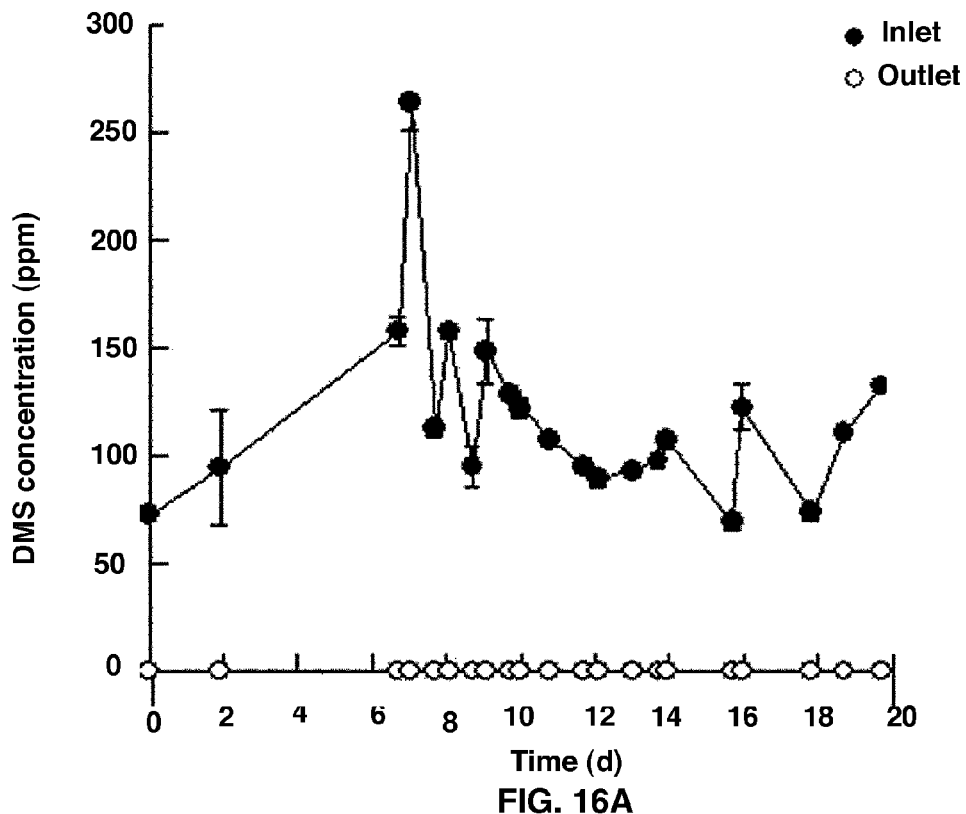
FIGS. 16A-16B are graphs showing inlet and outlet concentrations (FIG. 16A) of DMS in biofilter 3 and its efficiency of removal (FIG. 16B)
Figure 16B:
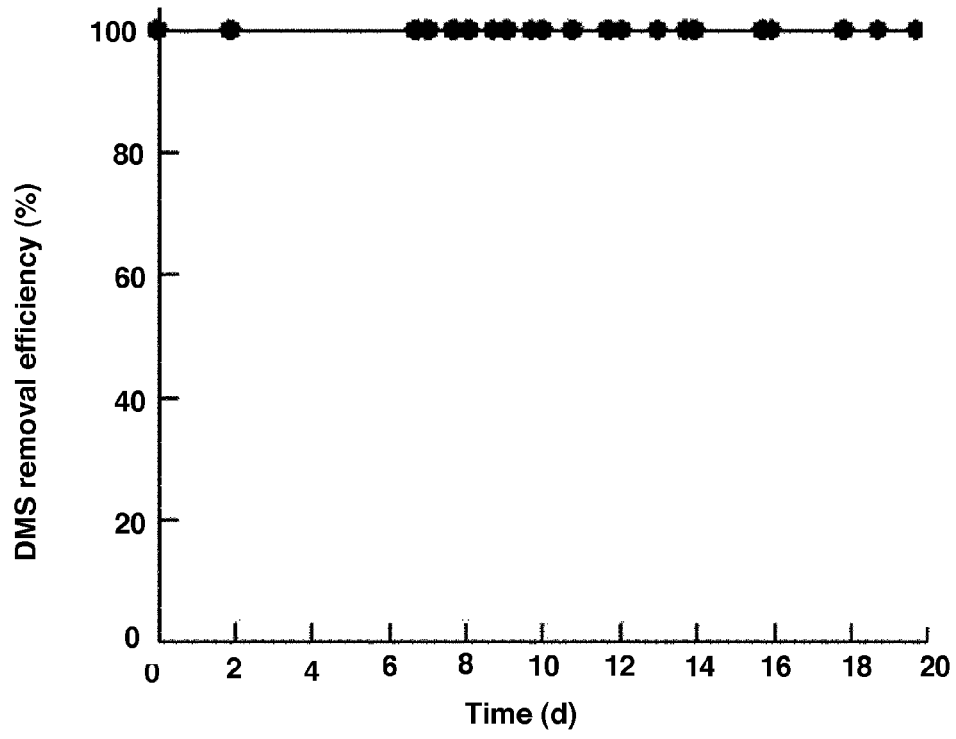
Figure 17A:
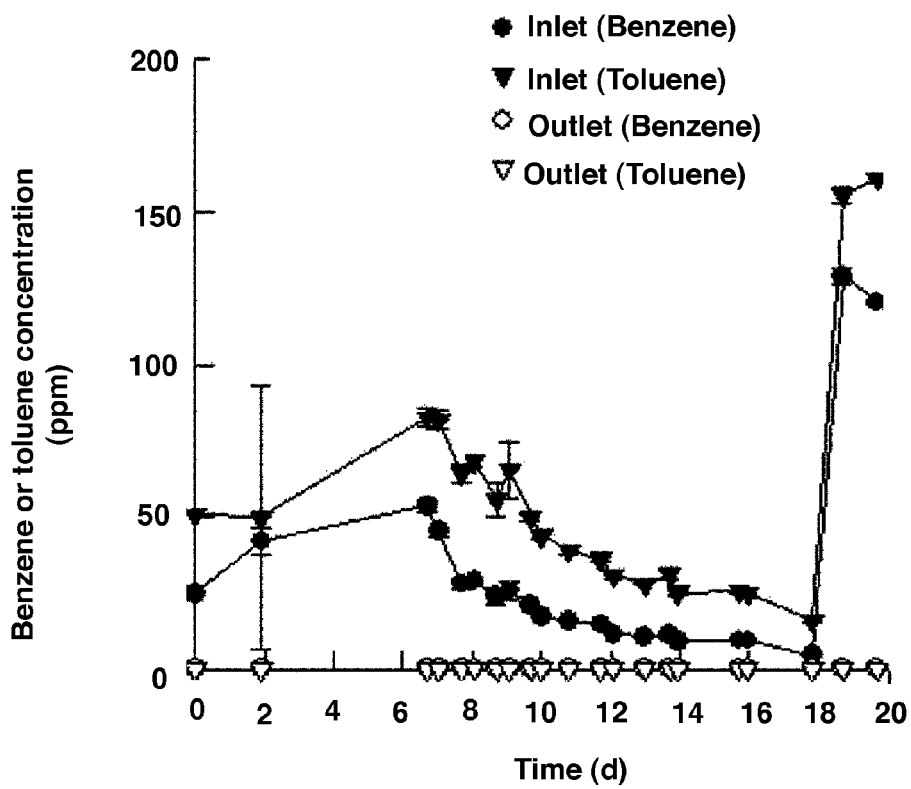
FIGS. 17A-17B are graphs showing inlet and outlet concentrations (FIG. 17B) of benzene or toluene in biofilter 3 and its efficiency of removal (FIG. 17B).
Figure 17B:
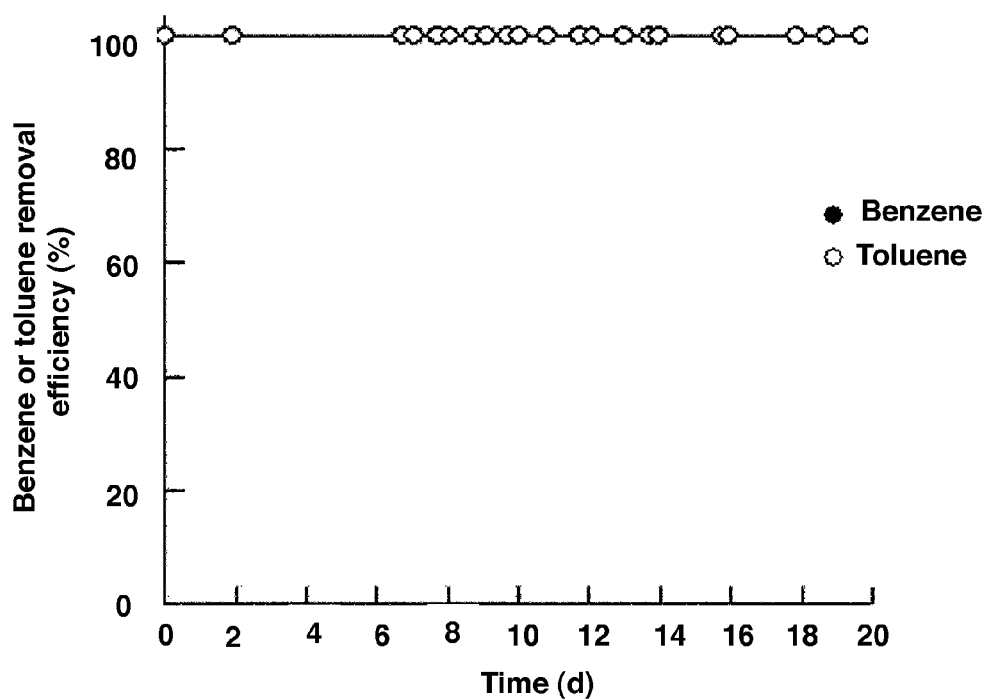

In biocover 3 supplied with all of methane, dimethyl sulfide, benzene and toluene, methane removal efficiency of less than 10% was observed at the beginning of the operation, but the efficiency increased over time and a methane removal efficiency of 60% or more was observed after 8 days. Even though the methane concentration at the inlet increased over time, a methane efficiency of 80% or more was stably maintained (FIG. 15). Dimethyl sulfide/benzene/toluene were completely removed at the beginning of the operation, and all of them were completely decomposed, even though the concentration at the inlet had been changed (FIGS. 16 and 17).

The metabolites of methane and dimethyl sulfide/benzene/toluene as carbon sources in each biofilter were investigated. Their balance was calculated, and shown in Table 4. The injection amounts of dimethyl sulfide, benzene, and toluene were 1/100 or less of the injection amount of methane, and thus disregarded.

TABLE 4

| Type of biofilter | Methane removed (%) | Generation of carbon dioxide by methane oxidation (%) [generation amount (presence of methane) - generation amount (absence of methane) |
|---|---|---|
| Biofilter 1 | 3.6% ± 0.07 | 3.7% ± 0.1 |
| Biofilter 2 | 4.0% ± 0.4 | 4.4% ± 1.4 |
| Biofilter 3 | 2.3% ± 0.07 | 2.3% ± 1.2 |

As shown in Table 4, 3.6% of methane was removed by biofilter 1, and the amount of carbon dioxide generated was 3.7%. 4% of methane was removed by biofilter 2, and the amount of carbon dioxide generated was 4% or more. 2.3% of methane was removed by biofilter 3, and the amount of carbon dioxide generated was 2.3%. The analysis of carbon dioxide concentrations showed that the carbons included in methane, dimethyl sulfide, toluene and benzene were completely oxidized to carbon dioxide in the biofilter (Table 4).

The metabolites of dimethyl sulfide as a sulfur source in each biofilter were investigated. Their balance was calculated. To analyze the metabolites resulting from the decomposition of dimethyl sulfide in biofilter 2 and biofilter 3, the qualitative/quantitative analysis of dissolved DMS metabolites such as DMSO and sulfate was performed, and the results are shown in Table 5.

TABLE 5

| Type of biofilter | DMS removed (S-mmole) | Sulfur compound in storage tank solution (mmole) | | Sulfur compounds in outlet gas (S-mmole) | | | Recovery rate (%) |
|---|---|---|---|---|---|---|---|
| | | Sulfate production | DMSO production | Residual DMS | MT production | Hydrogen sulfide production | |
| Biofilter 2 | 9.689 | 7.309 | 0.784 | 0 | 0 | 0 | 84 |
| Biofilter 3 | 4.617 | 3.906 | 0.915 | 0 | 0 | 0 | 103 |

As shown in Table 5, MT and hydrogen sulfide were not detected in the outlet gas, and 76% of the dimethyl sulfide injected was completely oxidized to sulfate in the storage tank of biofilter 2, and approximately 8% thereof was converted into DMSO, The recovery rate of sulfur was 84%, and 90% or more of dimethyl sulfide was oxidized to sulfate. Approximately 84% of the dimethyl sulfide injected was completely oxidized to sulfate in the storage tank of biofilter 3, and 19% thereof was converted into DMSO. The calculated recovery rate was 103%, and approximately 82% of dimethyl sulfide was oxidized to sulfate (Table 5).

In the biofilter of the present invention, dimethyl sulfide was decomposed according to the metabolic pathway of DMS-MT-hydrogen sulfide, rather than the conversion into DMSO, indicating that the final metabolites are completely oxidized to materials producing no odor, and thus the results are very significant in terms of odor removal.

Taken together, the biofilter inoculated with the *Sphingomonas* sp. MD2 strain capable of decomposing methane and dimethyl sulfide concurrently can be used to effectively reduce methane and dimethyl sulfide concurrently.

Effect of the Invention

According to the *Sphingomonas* sp. MD2 strain of the present invention and the method for decomposing methane or odor-producing compounds concurrently using the same, methane and odor can be effectively removed concurrently, and thus the cost required for separate treatment of methane and odor can be reduced, and methane and odor-producing compounds in landfills or the like can be effectively decomposed.

What is claimed is:

1. An isolated *Sphingomonas* sp. MD2 strain (KCTC 11845BP).

2. A composition for decomposing methane or odor-producing compounds, comprising an isolated *Sphingomonas* sp. MD2 strain (KCTC 11845BP) and a culture medium.

3. The composition according to claim 2, further comprising one or more fillers.

4. The composition according to claim 3, wherein the one or more fillers is soil, activated carbon, decomposed granite soil, or earthworm casting.

5. The composition according to claim 2, further comprising one or more methane-oxidizing bacteria.

6. The composition according to claim 5, wherein the one or more methane-oxidizing bacteria belongs to a genus of *Methylomonas, Methylomicrobium, Methylobacter, Methylocaldum, Methylophaga, Methylosarcina, Methylothermus, Methylohalobius, Methylosphaera, Methylocystis, Methylocella, Methylocapsa, Methylosinus,* or *Methylococcus*.

7. The composition according to claim 2, wherein the odor-producing compound is one or more of hydrogen sulfide, methyl mercaptan (methanethiol), dimethyl sulfide, benzene, or toluene.

8. A biocover for decomposing methane or odor-producing compounds, comprising the composition of claim 2 formed as a covering layer.

9. The biocover according to claim 8, further comprising an oxygen-releasing compound.

10. The biocover according to claim 9, wherein the oxygen-releasing compound is magnesium peroxide, calcium peroxide or sodium percarbonate.

11. A biofilter for decomposing methane or odor-producing compounds, comprising the composition of claim 2 and a support to which the composition adheres.

12. The biofilter according to claim 11, further comprising an oxygen releasing compound.

13. The biofilter according to claim 12, wherein the oxygen releasing compound is magnesium peroxide, calcium peroxide or sodium percarbonate.

14. A method for decomposing methane or odor-producing compounds, comprising the steps of treating a source of generation of methane or odor-producing compounds with the composition of claim 2; and decomposing the methane or odor-producing compounds by the composition.

15. The method according to claim 14, wherein the source of the generation of methane or odor-producing compounds is scrap landfills, waste landfills, wastewater treatment facilities, manure treatment facilities, livestock wastewater treatment facilities, food waste treatment facilities, petrochemical product-manufacturing factories, sewage treatment facilities, industrial wastewater treatment facilities, livestock farms, food-processing plants, paint-manufacturing plants, casting-manufacturing plants, petroleum-refining facilities, slaughterhouses, fertilizer-producing factories, combustion facilities for plastic product manufacture, coating facilities or plating factories.

16. A system for biologically decomposing methane or odor-producing compounds comprising a bioactive layer installed at a source of generation of methane or odor-producing compounds, wherein the bioactive layer comprises:
one or more biocovers of claim 8 laminated together; and
a ventilating layer surrounding the biocover layer or a ventilating layer laminated onto the lower surface of the biocover layer.

17. The system according to claim 16, wherein the source of the generation of methane or odor-producing compounds is scrap landfills, waste landfills, wastewater treatment facilities, manure treatment facilities, livestock wastewater treatment facilities, food waste treatment facilities, petrochemical product-manufacturing factories, sewage treatment facilities, industrial wastewater treatment facilities, livestock farms, food-processing plants, paint-manufacturing plants, casting-manufacturing plants, petroleum-refining facilities, slaughterhouses, fertilizer-producing factories, combustion facilities for plastic product manufacture, coating facilities or plating factories.

18. A system for biologically decomposing methane or odor-producing compounds comprising a bioactive layer installed in a source of generation of methane or odor-producing compounds, wherein the bioactive layer comprises:
a biofilter layer formed by laminating one or more biofilters of claim 11; and a ventilating layer surrounding the biofilter layer or a ventilating layer laminated on the lower surface of the biofilter layer.

19. The system according to claim 18, wherein the source of the generation of methane or odor-producing compounds is scrap landfills, waste landfills, wastewater treatment facilities, manure treatment facilities, livestock wastewater treatment facilities, food waste treatment facilities, petrochemical product manufacturing factories, sewage treatment facilities, industrial wastewater treatment facilities, livestock farms, food processing plants, paint manufacturing plants, casting manufacturing plants, petroleum refining facilities, slaughterhouses, fertilizer producing factories, combustion facilities for plastic product manufacture, coating facilities or plating factories.

* * * * *